(12) United States Patent
O'Brien et al.

(10) Patent No.: US 10,976,246 B2
(45) Date of Patent: Apr. 13, 2021

(54) SPECTROSCOPIC CHARACTERIZATION OF SEAFOOD

(71) Applicant: VIAVI Solutions Inc., San Jose, CA (US)

(72) Inventors: Nada A. O'Brien, Santa Rosa, CA (US); Charles A. Hulse, Sebastopol, CA (US); Heinz W. Siesler, Essen (DE); Changmeng Hsiung, Redwood City, CA (US)

(73) Assignee: VIAVI Solutions Inc., San Jose, CA (US)

( * ) Notice: Subject to any disclaimer, the term of this patent is extended or adjusted under 35 U.S.C. 154(b) by 0 days.

(21) Appl. No.: 16/527,712

(22) Filed: Jul. 31, 2019

(65) Prior Publication Data
US 2019/0353587 A1    Nov. 21, 2019

Related U.S. Application Data

(63) Continuation of application No. 15/131,654, filed on Apr. 18, 2016, now Pat. No. 10,401,284, which is a
(Continued)

(51) Int. Cl.
*G01N 21/359* (2014.01)
*G01J 3/26* (2006.01)
(Continued)

(52) U.S. Cl.
CPC .......... *G01N 21/359* (2013.01); *G01J 3/0216* (2013.01); *G01J 3/26* (2013.01);
(Continued)

(58) Field of Classification Search
CPC ...... G01N 21/359; G01N 21/55; G01N 21/27; G01N 33/12; G01N 21/3563;
(Continued)

(56) References Cited

U.S. PATENT DOCUMENTS

| | | |
|---|---|---|
| 5,539,207 A | 7/1996 | Wong et al. |
| 6,649,412 B1 | 11/2003 | Borggaard et al. |

(Continued)

FOREIGN PATENT DOCUMENTS

| | | |
|---|---|---|
| CN | 101059424 A | 10/2007 |
| CN | 101620178 A | 1/2010 |

(Continued)

OTHER PUBLICATIONS

Cozzolino et al., A Review on the Application of Infrared Technologies to Determine and Monitor Composition and Other Quality Characteristics in Raw Fish, Fish Products, and Seafood, 2012, Applied Spectroscopy Reviews, vol. 47, pp. 207-218. (Year: 2012).*
(Continued)

*Primary Examiner* — Christine S. Kim
(74) *Attorney, Agent, or Firm* — Harrity & Harrity, LLP

(57) ABSTRACT

A method and apparatus for field spectroscopic characterization of seafood is disclosed. A portable NIR spectrometer is connected to an analyzer configured for performing a multivariate analysis of reflection spectra to determine qualitatively the true identities or quantitatively the freshness of seafood samples.

20 Claims, 20 Drawing Sheets

Related U.S. Application Data continuation of application No. 14/222,216, filed on Mar. 21, 2014, now Pat. No. 9,316,628.

(60) Provisional application No. 61/804,106, filed on Mar. 21, 2013.

(51) Int. Cl.

| | |
|---|---|
| G01J 3/28 | (2006.01) |
| G01J 3/02 | (2006.01) |
| G01N 21/3563 | (2014.01) |
| G01N 33/12 | (2006.01) |
| G01N 21/27 | (2006.01) |
| G01N 21/55 | (2014.01) |
| G01J 3/12 | (2006.01) |

(52) U.S. Cl.
CPC ............ *G01J 3/2803* (2013.01); *G01N 21/27* (2013.01); *G01N 21/3563* (2013.01); *G01N 21/55* (2013.01); *G01N 33/12* (2013.01); *G01J 2003/1234* (2013.01); *G01J 2003/2873* (2013.01); *G01N 2201/0221* (2013.01); *G01N 2201/061* (2013.01); *G01N 2201/12* (2013.01)

(58) Field of Classification Search
CPC ......... G01N 2201/12; G01N 2201/061; G01N 2201/0221; G01N 21/01; G01J 3/0216; G01J 3/2803; G01J 3/26; G01J 2003/2873; G01J 2003/1234
See application file for complete search history.

(56) References Cited

U.S. PATENT DOCUMENTS

| | | | |
|---|---|---|---|
| 7,420,663 B2* | 9/2008 | Wang | G01J 3/02 356/72 |
| 7,728,296 B2 | 6/2010 | Cole et al. | |
| 7,750,299 B2 | 7/2010 | Monro et al. | |
| 9,316,628 B2 | 4/2016 | O'Brien et al. | |
| 2003/0023148 A1 | 1/2003 | Lorenz et al. | |
| 2003/0032064 A1 | 2/2003 | Soller et al. | |
| 2004/0146615 A1 | 7/2004 | McDonald et al. | |
| 2007/0262257 A1 | 11/2007 | Monro et al. | |
| 2009/0220189 A1 | 9/2009 | Kiesel et al. | |
| 2010/0309454 A1 | 12/2010 | Zhang et al. | |
| 2011/0273709 A1 | 11/2011 | Sweeney et al. | |
| 2012/0153221 A1 | 6/2012 | Wauters et al. | |
| 2014/0320858 A1* | 10/2014 | Goldring | G01J 3/0256 356/416 |
| 2015/0330906 A1 | 11/2015 | Wakita et al. | |
| 2016/0231237 A1 | 8/2016 | O'Brien et al. | |

FOREIGN PATENT DOCUMENTS

| | | |
|---|---|---|
| TW | 201236734 A | 9/2012 |
| WO | 2007000165 A1 | 1/2007 |

OTHER PUBLICATIONS

Uddin M., et al., "Non-destructive Visible/NIR Spectroscopy for Differentiation of Fresh and Frozen-thawed Fish," Journal of Food Science, 2005, vol. 70 (8), pp. C506-C510.

Balanbin R.M., et al., Support Vector Machine Regression (SVR/LS-SVM)—An Alternative to Neural Networks (ANN) for Analytical Chemistry? Comparison of Nonlinear Methods on Near Infrared (NIR) Spectroscopy Data, Feb. 25, 2011, Royal Society of Chemistry, vol. 136, pp. 1703-1712.

Berrueta L.A., et al., "Supervised Pattern Recognition in Food Analysis,"Journal of Chromatography A, 2007, vol. 1158, pp. 196-214, Retrieved from the Internet: URL: www.researchgate.net/publication/6296688_supervised_pattern_recognition_in_food_analysis/file/9fcfd5. . . .

Bryce, E., Like Shazam, but for Fish, Jun. 7, 2016, Hakai Magazine, pp. 1-3.

Buck E.H., "Congressional Research Service Report for Congress, Seafood Marketing: Combating Fraud and Deception," www.crs.gov, RL-34124, Jul. 2, 2010, 15 pages.

Costa C., et al., "Application of Non-invasive Techniques to Differentiate Sea Bass (*Dicentrarchus labrax*, L. 1758) Quality Cultured Under Different Conditions," Aquacult Int, Nov. 18, 2010, vol. 19, pp. 765-778.

Cozzolino D., et al., "Usefulness of Near-Infrared Reflectance (NIR) Spectroscopy and Chemometrics to Discriminate Fishmeal Batches Made with Different Fish Species," Journal of Agricultural and Food Chemistry, Apr. 25, 2005, vol. 53, pp. 4459-4463.

Downey G., "Non-invasive and Non-destructive Analysis of Farmed Salmon Flesh by Near Infra-red Spectroscopy," Food Chemistry, 1996, vol. 55, pp. 305-311.

Extended European Search Report for Application No. EP14779143, dated Oct. 18, 2016, 5 pages.

Fasolato L., et al., "Application of Nonparametric Multivariate Analyses to the Authentication of Wild and Farmed European Sea Bass (*Dicentrarchus labrax*)," Results of a Survey on Fish Sampled in the Retail Trade, Sep. 21, 2010, vol. 58, pp. 10979-10988.

Gayo J., et al., "Detection and Quantification of Species Authenticity and Adulteration in Crabmeat Using Visible and Near-Infrared Spectroscopy," Journal of Agricultural and Food Chemistry, Feb. 7, 2007, pp. 585-592.

International Search Report and Written Opinion for Application No. PCT/US2014/031369, dated Aug. 1, 2014, 12 pages.

Jorgensen A., "Clustering Excipient near Infrared Spectra using Different Chemometirc Methods," 12 pages.

Majolini D., et al., "Near Infrared Reflectance Spectroscopy (NIRS) Characterization of European Sea Bass (*Dicentrarchus labrax*) from Different Rearing Systems," Italian Journal of Animal Science, 2009, vol. 8, pp. 860-862.

Menze B.H., et al., "A Comparison of Random Forest and its Gini Importance with Standard Chemometric Methods for the Feature Selection and Classification of Spectral Data,"BMC Bioinformatics, Jul. 10, 2009, vol. 10(1), 16 pages, Retrieved from the Internet: URL: http://www.biomedcentral.com/content/pdf/1471-2105-10-213.pdf.

Nilsen H., et al., "Visible/Near Infrared Spectroscopy: A New Tool for the Evaluation of Fish Freshness?," Journal of Food Science, May 2002, pp. 1-6.

NIR on thego 2010, "Universita degli Studi di Padova," 2010, pp. 11, 12, 22, 28, 36, 37, 47, 49, and 74-76, Retrieved from the Internet: URL: http://www.grainit.it/NIRontheGO/Atti.pdf.

O'Brien N.A., et al., "Miniature Near-infrared (NIR) Spectrometer Engine for Handheld Applications ," Next-Generation Spectroscopic Technology V, SPIE, May 11, 2012, vol. 8374(1), XP060003026, 8 pages.

Ottavian M., et al., "Use of Near-Infrared Spectroscopy for Fast Fraud Detection in Seafood: Application to the Authentication of Wild European Sea Bass (*Dicentrarchus labrax*)," Journal of Agricultural and Food Chemistry, Dec. 11, 2011, vol. 60, pp. 639-648.

Sigernes F., et al., "Assessment of Fish (cod) Freshness by VIS/NIR Spectroscopy," available online on Jul. 27, 2002, 6 pages.

Uddin M., et al, "Applications of Vibrational Spectroscopy to the Analysis of Fish and Other Aquatic Food Products", Nov. 15, 2010, Handbook of Vibrational Spectroscopy, pp. 1-21.

Warner K., et al., "Oceana Study Reveals Seafood Fraud Nationwide," Feb. 2013 report, 69 pages.

Xiccato G., et al., "Prediction of Chemical Composition and Origin Identification of European Sea Bass (*Dicentrarchus Labrax* L.) by near Infrared Reflectance Spectroscopy (NIRS)," Food Chemistry, Jun. 2004, vol. 86, pp. 275-281.

(56) References Cited

OTHER PUBLICATIONS

Zhu F., et al., "Application of Visible and Near Infrared Hyperspectral Imaging to Differentiate Between Fresh and Frozen-Thawed Fish Fillets," Food and Bioprocess Technology, Mar. 21, 2012, vol. 6(10), pp. 2931-2937.
Corresponding U.S. Appl. No. 15/131,654, filed Apr. 18, 2016.

* cited by examiner

SPECTROSCOPIC CHARACTERIZATION OF SEAFOOD

CROSS-REFERENCE TO RELATED APPLICATIONS

This application is a continuation of U.S. patent application Ser. No. 15/131,654, filed Apr. 18, 2016, which is a continuation of U.S. patent application Ser. No. 14/222,216, filed Mar. 21, 2014 (now U.S. Pat. No. 9,316,628), which claims priority from U.S. Provisional Application No. 61/804,106, filed Mar. 21, 2013, the contents of which are incorporated herein by reference.

TECHNICAL FIELD

The present invention relates to materials characterization and identification, and in particular to spectroscopic characterization of seafood.

BACKGROUND OF THE INVENTION

A recently published report on one of the largest surveys conducted to date about seafood fraud revealed that one third of seafood species purchased at restaurants and grocery stores in cities across the United States were mislabeled. The study was conducted by Oceana, a non-profit international advocacy group, over a period of 2 years from 2010-2012, whereby over 1200 samples were collected from 674 retail outlets in 21 US states (K. Warner, W. Timme, B. Lowell, and M. Hirshfield, "Oceana Study Reveals Seafood Fraud Nationwide", February 2013 report). DNA testing was performed on fish samples to correctly identify the fish species and uncover mislabeling. Similar conclusions could be drawn from a previous US Congressional Research Service Report regarding combating fraud and deception in seafood marketing (Congressional Research Service Report for Congress, 7-5700, www.crs.gov, RL-34124 (2010)).

Substitution of a more expensive fish by a lower-cost species is illegal. It is motivated by monetary gains by perpetrators leading to negative economic, health, and environmental consequences. Consumers and honest seafood suppliers are cheated into paying higher prices for lower-cost, less-desirable substitutes. One of most commonly substituted and more expensive fish is red snapper often swapped for tilapia. Furthermore, some fish substitutes pose health hazards. For example, the above Oceana study has determined that over 90% of what is advertised as white tuna was actually escolar, which is a snake mackerel species containing toxins known to cause gastrointestinal problems. Lastly, some substituted fish may be of an overfished or threatened species. One such fish is the Atlantic cod, which was found to be swapped for Pacific cod in the same study.

The supply chain "from boat to plate" is complex and unregulated, making such illegal activities difficult to track. Combating fish fraud requires traceability of fish supply across the entire supply chain, as well as and increased inspection. DNA testing for inspection is time consuming and can only be done on a sampling basis. The DNA testing requires taking samples of fish to a lab and waiting for results,—a process that can take days.

Wong in U.S. Pat. No. 5,539,207 discloses a method of identifying human or animal tissue by Fourier Transform Infrared (FT-IR) spectroscopy. A mid-infrared spectrum of a tissue in question is measured and compared to a library of infrared spectra of known tissues, to find a closest match. Either a visual comparison, or a pattern recognition algorithm can be used to match the infrared spectra. In this way, various tissues, and even normal or malignant (e.g. cancerous) tissues can be identified.

Detrimentally, the method of Wong is difficult to use for the purpose of seafood identification in field conditions. An FT-IR spectrometer is a complex and bulky optical device. Its core module, a scanning Michelson interferometer, uses a precisely movable large optical mirror to perform a wavelength scan. To stabilize the mirror, a heavy optical bench is used. Due to many precision optical and mechanical components, an FT-IR spectrometer requires laboratory conditions, and needs to be re-calibrated and re-aligned frequently by trained personnel. The use of an FT-IR spectrometer is dictated by the fact that the fundamental vibrational frequencies of the infrared fingerprint are present in the 2.5 to 5 micrometers region of the electromagnetic spectrum. These vibrational bands are of high resolution and high absorption levels, showing strong absorption with narrow spectral bands.

Monro in U.S. Pat. No. 7,750,299 discloses a system for active biometric spectroscopy, in which a DNA film of a particular biological subject is irradiated by a frequency-tunable millimeter-wave radio transmitter, and radio waves transmitted and scattered by the DNA film are detected. Monro teaches that radio wave scattering spectra of different DNA films are different. Therefore, transmitted or scattered radio wave spectrum can detect different DNA films, which can be associated with different fish species. In this way, species of a fish sample can be identified.

Detrimentally, the method of Monro cannot be applied to the fish samples themselves, because the signal from non-DNA tissues will overwhelm the DNA signal. Because of this, DNA of the fish samples have to be extracted and formed into a film. The sample preparation is time-consuming, and can only be done in lab conditions.

Cole et al. in U.S. Pat. No. 7,728,296 disclose an apparatus and method for detection of explosive materials using terahertz (THz) radiation. THz radiation occupies a frequency band between infrared and millimeter radio waves. Many explosive materials have a unique spectral signature in THz frequency domain, thus affording a non-invasive, remote detection of explosives with a high sensitivity. Detrimentally, THz radiation sources are bulky and expensive, limiting their current use to security-critical applications such as at airport security checkpoints.

The methods and devices of the prior art appear unsuitable for a goal of identification of seafood species in field conditions. A method and system are required that would enable a food and drug administration (FDA) official perform a quick on-the-spot seafood species identification and characterization, assisting the official in deciding whether to take a law enforcement action. Private persons, such as restaurant chefs, sushi bar patrons, and fish market customers, would also benefit from a possibility to quickly verify seafood species being purchased.

SUMMARY OF THE INVENTION

It is a goal of the invention to provide a method and apparatus for field spectroscopic characterization of seafood.

From the technology standpoint, it is preferable to perform spectroscopic measurements in wavelength bands that afford easy generation, wavelength separation, and detection of electromagnetic radiation. A near infrared (NIR) band, e.g. between 0.7 and 2.5 micrometers, satisfies this condition. Broadband light emitting diodes and even miniature incandescent sources can be used for generation of NIR light in this wavelength band. A variety of spectrally selective elements, e.g. thin-film interference filters, are available for wavelength separation. Photodiode arrays are available for detection of NIR light.

Despite the convenience of working in the NIR part of the spectrum, the prior art has been largely focusing on longer, less technology-friendly wavelength bands, because main vibrational frequencies of characteristic molecular bonds of most organic compounds correspond to wavelengths longer than 2.5 micrometers (2500 nm), necessitating the use of heavy and bulky equipment to generate, wavelength-disperse, and detect electromagnetic radiation at these longer wavelengths. The inventors have realized that the multiples of the vibrational frequencies, or so called overtones, do fall within the technology-convenient NIR band and, therefore, biological substance identification information is present in the NIR spectra, although this information is hidden due to a relatively low amplitude and multiple frequencies of the overtones.

When spectroscopic information is not readily available or visually identifiable from a spectrum, advanced data processing and feature or pattern extraction and modeling techniques, such as Principle Component Analysis (PCA), Soft Independent Modeling of Class Analogy (SIMCA), Partial Least Square Discriminant Analysis (PLS-DA), and Support Vector Machine (SVM), can be used to extract the required information. Therefore, the multivariate pattern recognition and data regression enables the use of a lightweight and compact NIR spectrometer for identification and characterization of seafood species.

In accordance with the invention, there is provided a method for field authentication of a seafood sample, comprising:

(a) providing a portable NIR spectrometer;
(b) obtaining a reflection spectrum of the seafood sample using the NIR spectrometer of step (a);
(c) performing a multivariate pattern recognition analysis of the reflection spectrum of the seafood sample obtained in step (b) to determine a matching spectrum with a most similar spectral pattern by comparing the reflection spectrum to a library of known identity spectra corresponding to different species of seafood; and
(d) identifying the seafood sample based on the matching spectrum bearing the most similar spectral pattern determined in step (c).

These pattern recognition algorithms can also generate a confidence measure, or a probability estimate, of a likelihood of the identification result.

In accordance with the invention, there is further provided a method for field determination of freshness of a seafood sample, comprising:

(a) providing a portable NIR spectrometer;
(b) obtaining a reflection spectrum of the seafood sample using the NIR spectrometer of step (a);
(c) performing a multivariate pattern recognition analysis of the reflection spectrum of the seafood sample obtained in step (b) to determine a matching spectrum with a most similar spectral pattern by comparing the reflection spectrum to a library of known identity spectra corresponding to the freshness of the seafood sample, thereby providing a quantitative measure of the freshness of the seafood sample.

The reflection spectrum can be obtained from a plurality of locations on the seafood sample to reduce the effect of surface texture of the seafood sample. The multivariate regression analysis can include e.g. Partial Least Square (PLS) and Support Vector Regression (SVR).

In accordance with the invention, there is further provided an apparatus for field authentication of a seafood sample, comprising:

a portable NIR spectrometer for obtaining a NIR reflection spectrum of the seafood sample, and an analyzer operationally coupled to the spectrometer and configured for performing a multivariate pattern recognition analysis of the reflection spectrum of the seafood samples to determine a matching spectrum with a most similar spectral pattern by comparing the reflection spectrum to a library of known identity spectra corresponding to different species of seafood, and to identify the seafood sample based on the matching spectrum bearing the most similar spectral pattern.

The portable NIR spectrometer can include a spectrally laterally variable optical transmission filter coupled to a photodetector array, resulting in a particularly compact and lightweight structure. A mobile communication device can be configured to communicate with the NIR spectrometer and perform the multivariate analysis of the reflection spectra obtained by the portable NIR spectrometer. Furthermore, at least some data analysis and spectra pattern models building activities can be performed at a remote server in communication with the mobile device.

In accordance with yet another aspect of the invention, there is further provided a non-transitory storage medium disposed in the mobile communication device and having encoded thereon the library of the known identity spectra.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Exemplary embodiments will now be described in conjunction with the drawings, in which.

Figure 9:
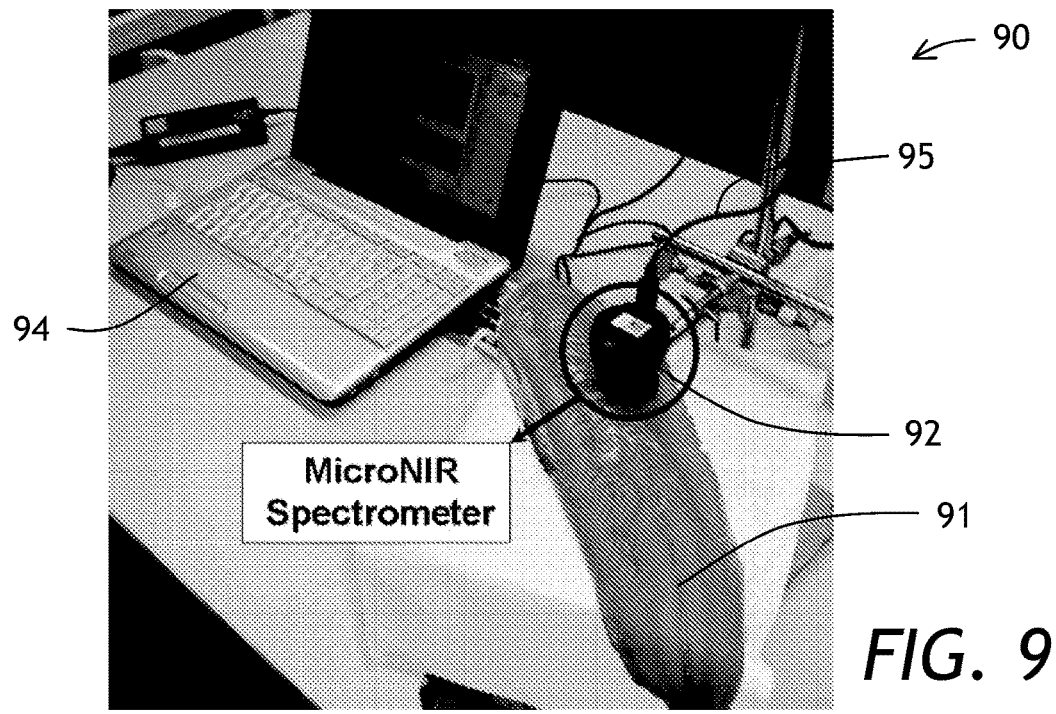
Figures 10A, 10B:
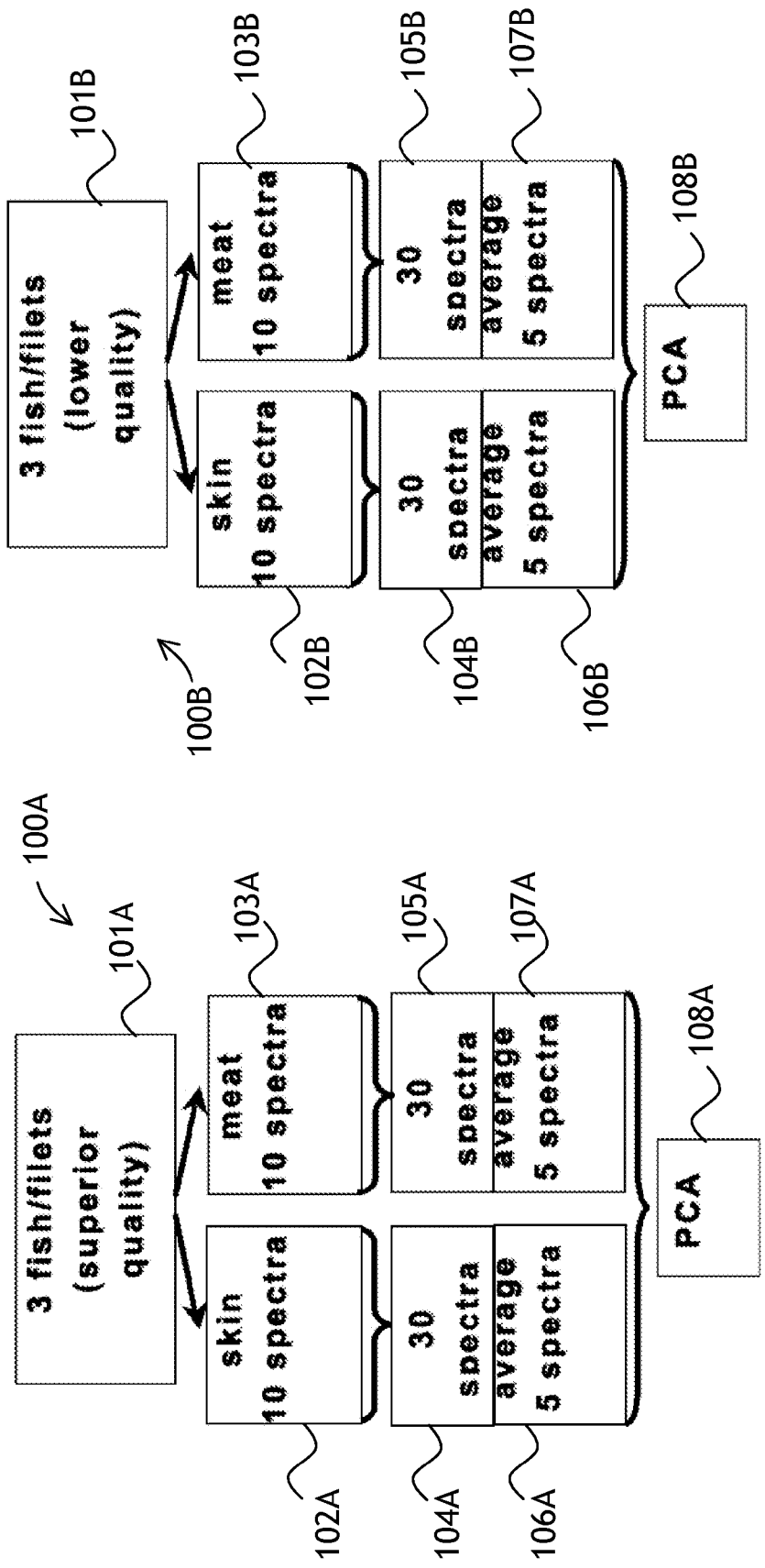
Figure 11:
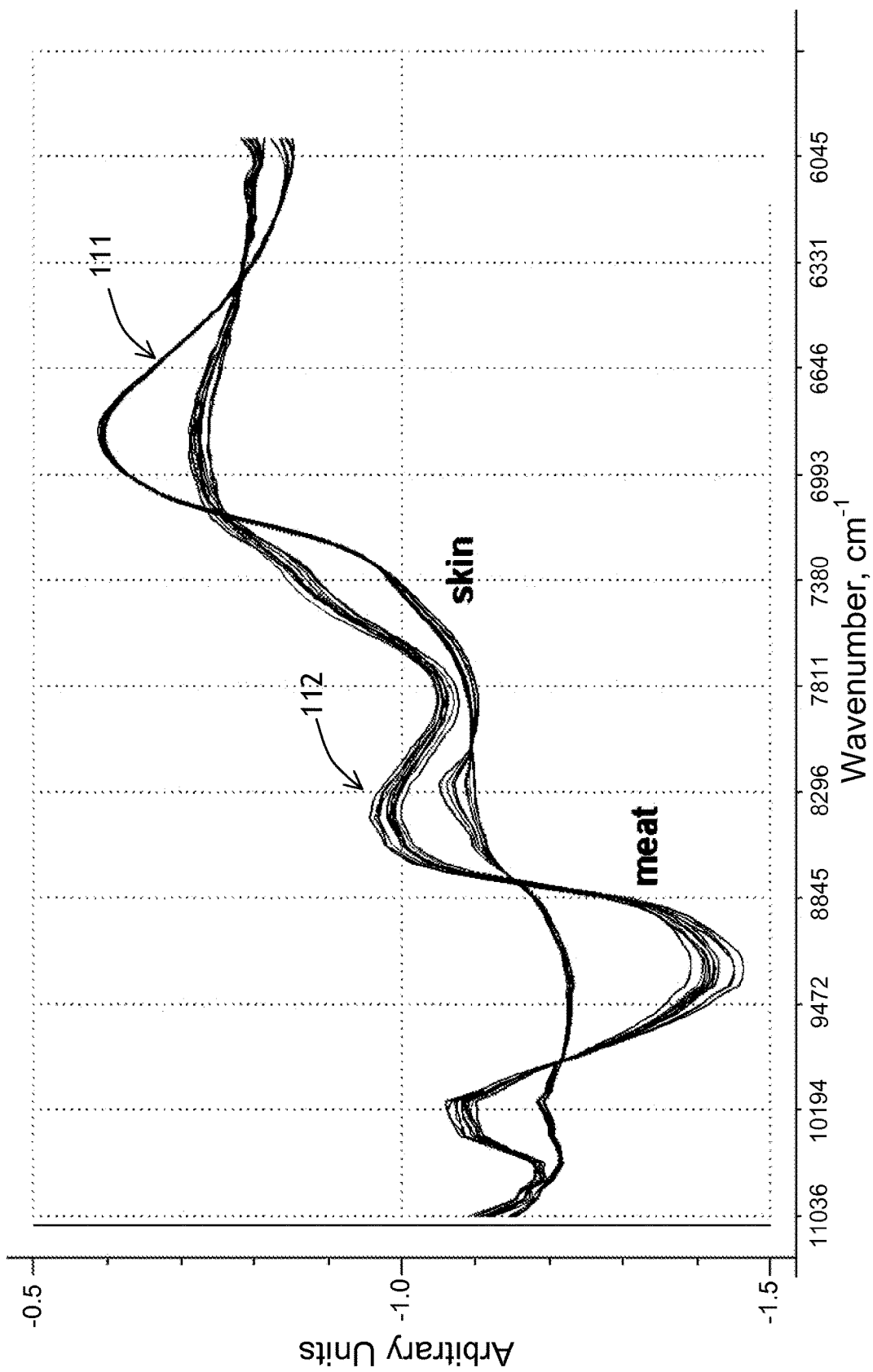
Figure 12:
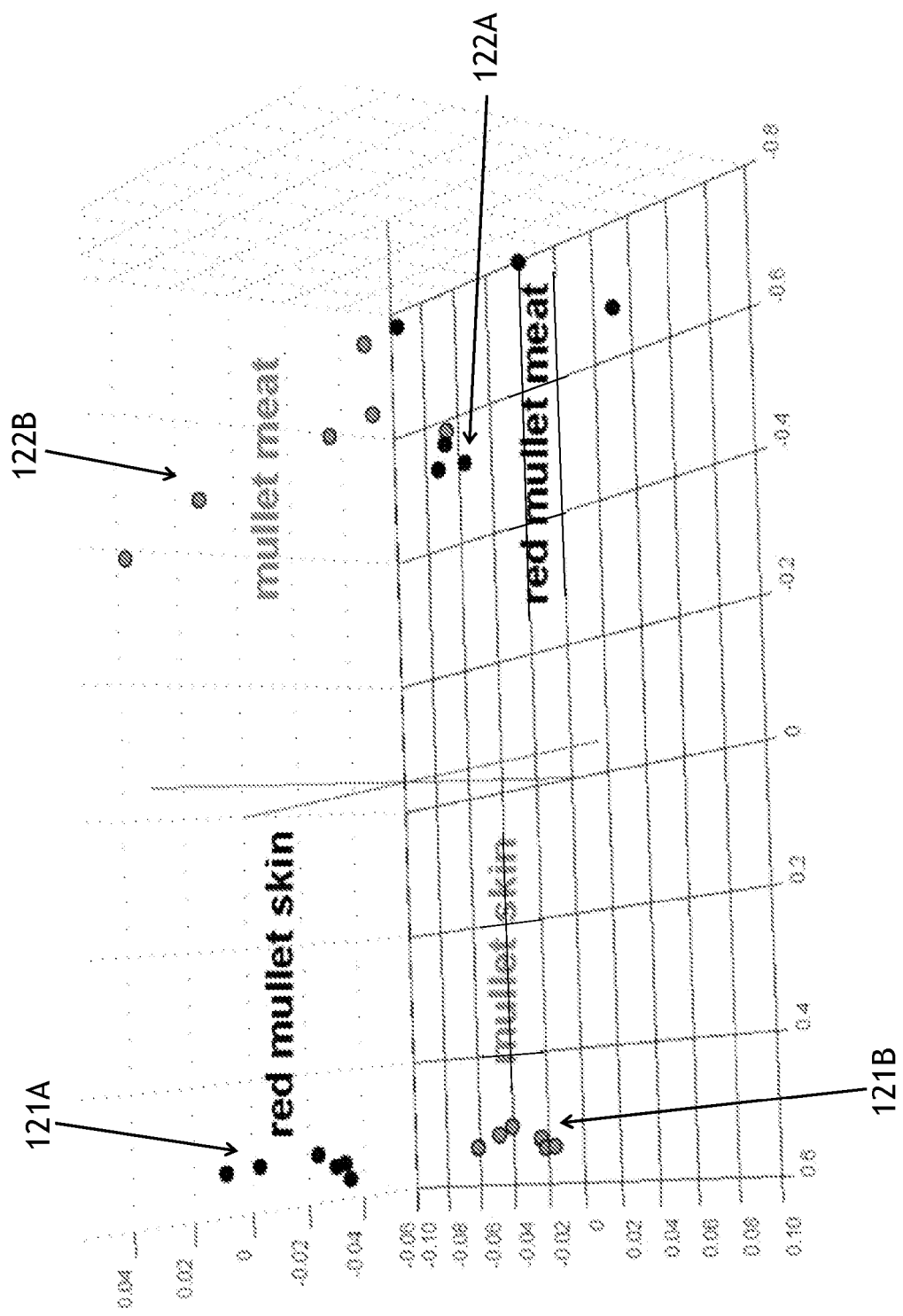
Figure 13A:
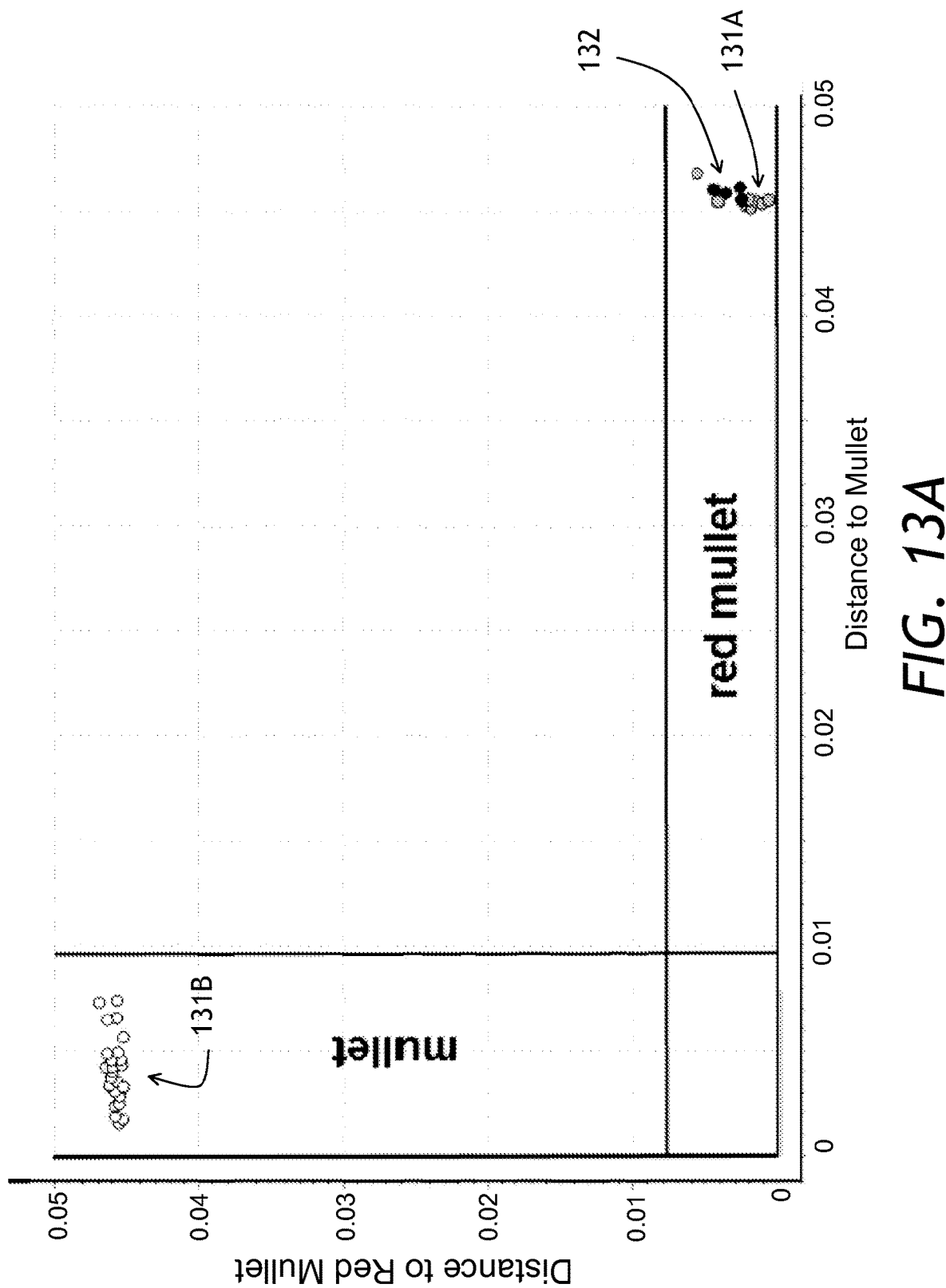
Figure 14:
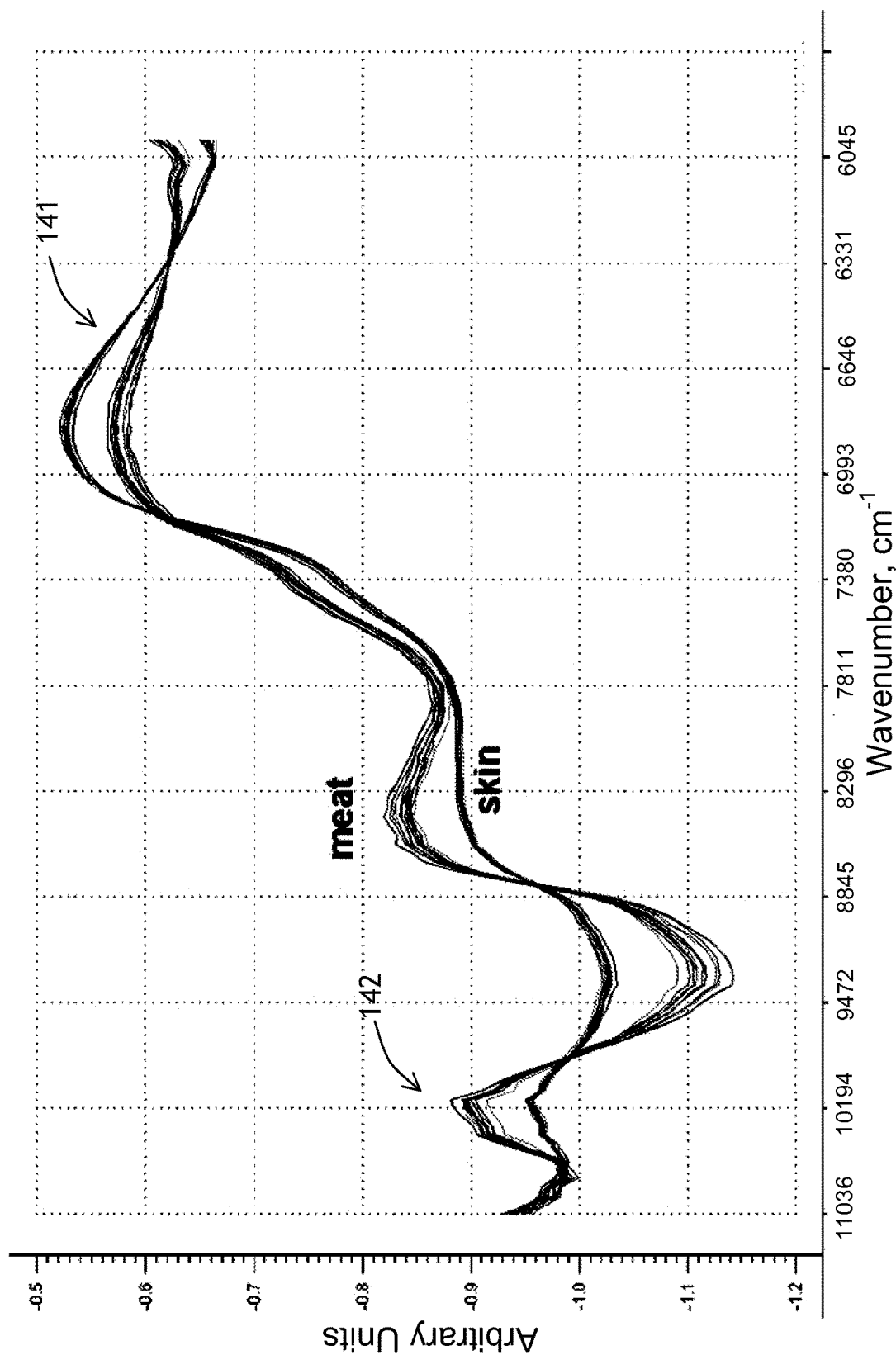
Figure 15:
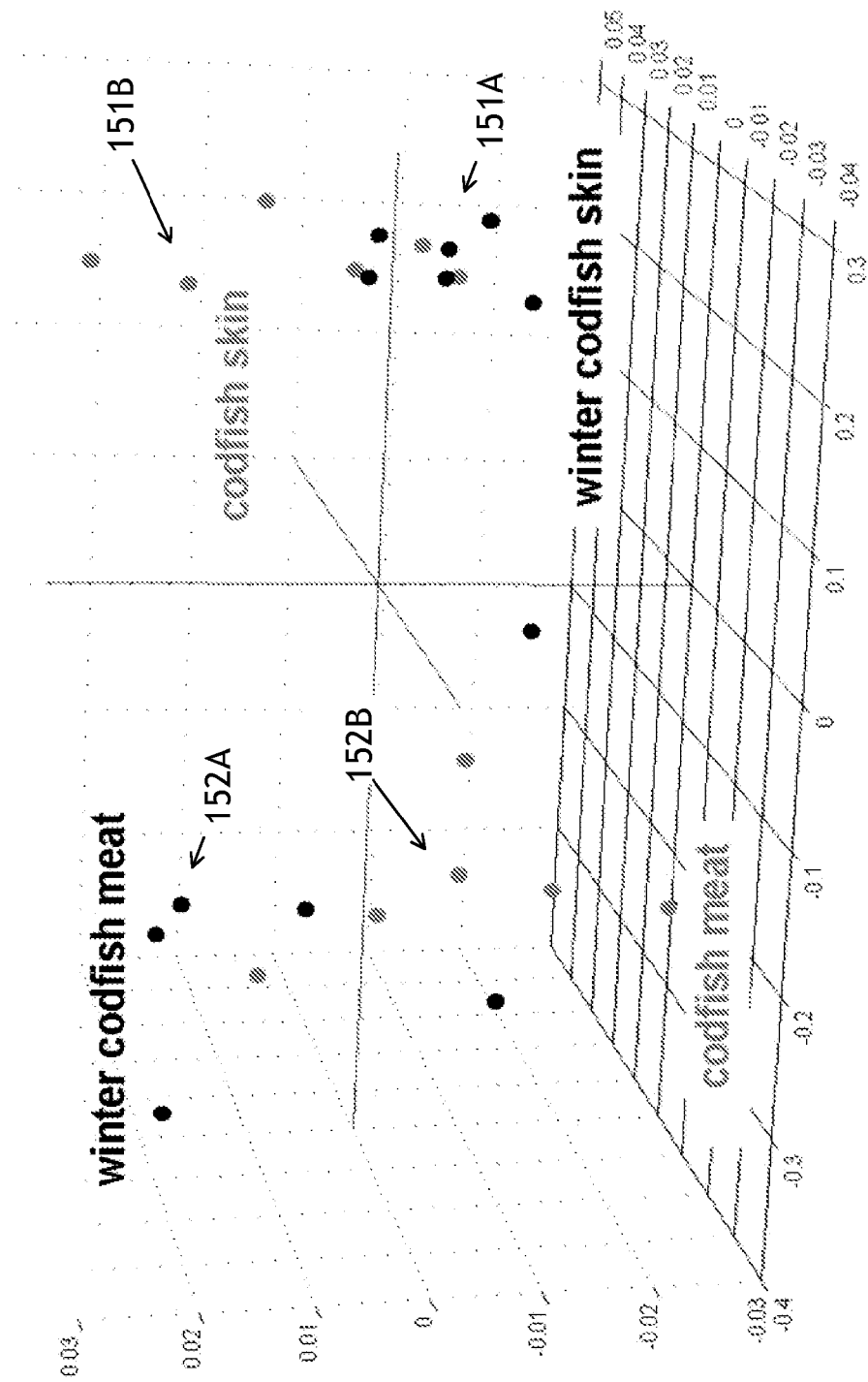
Figure 17:
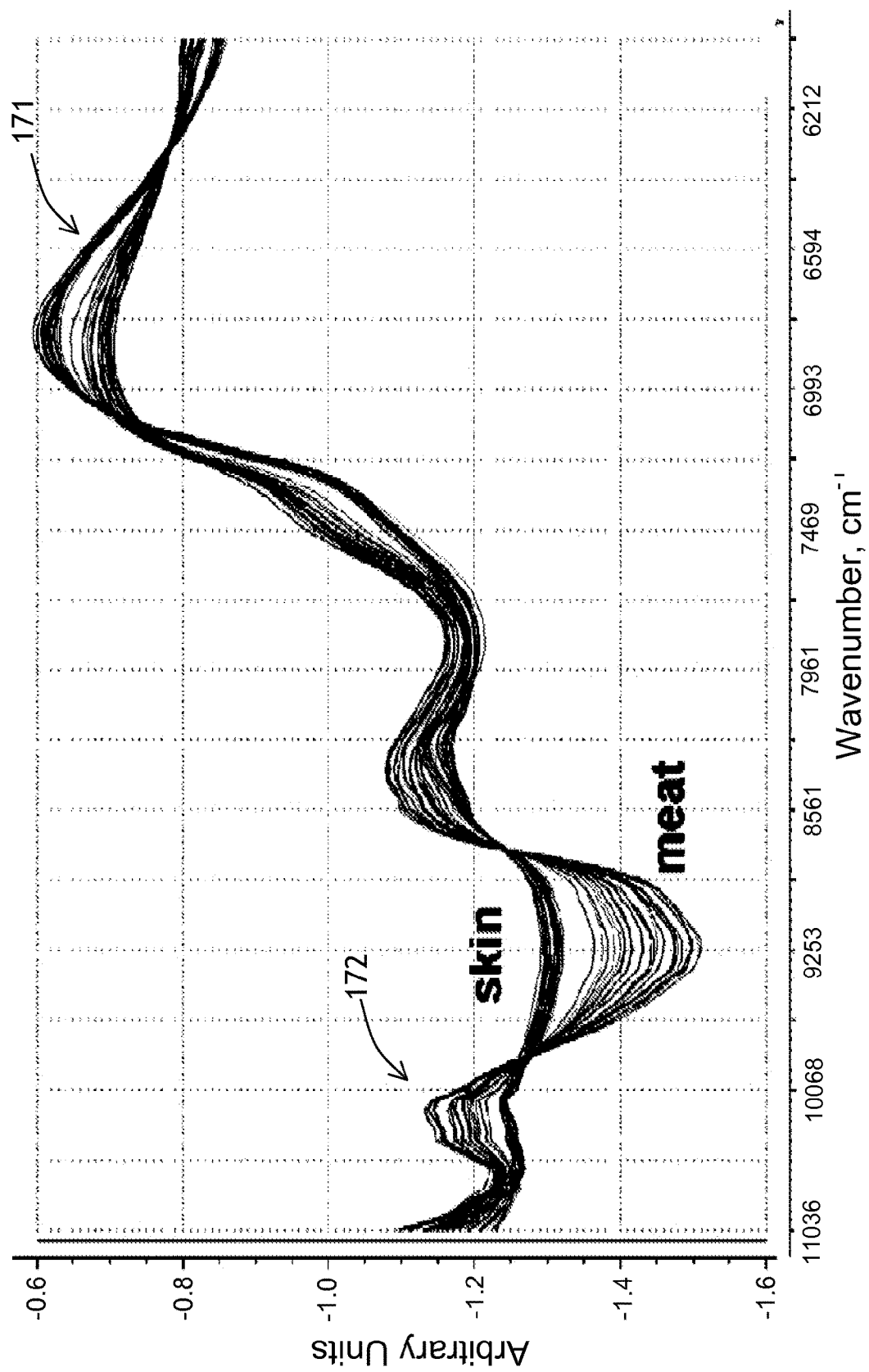
Figure 18:
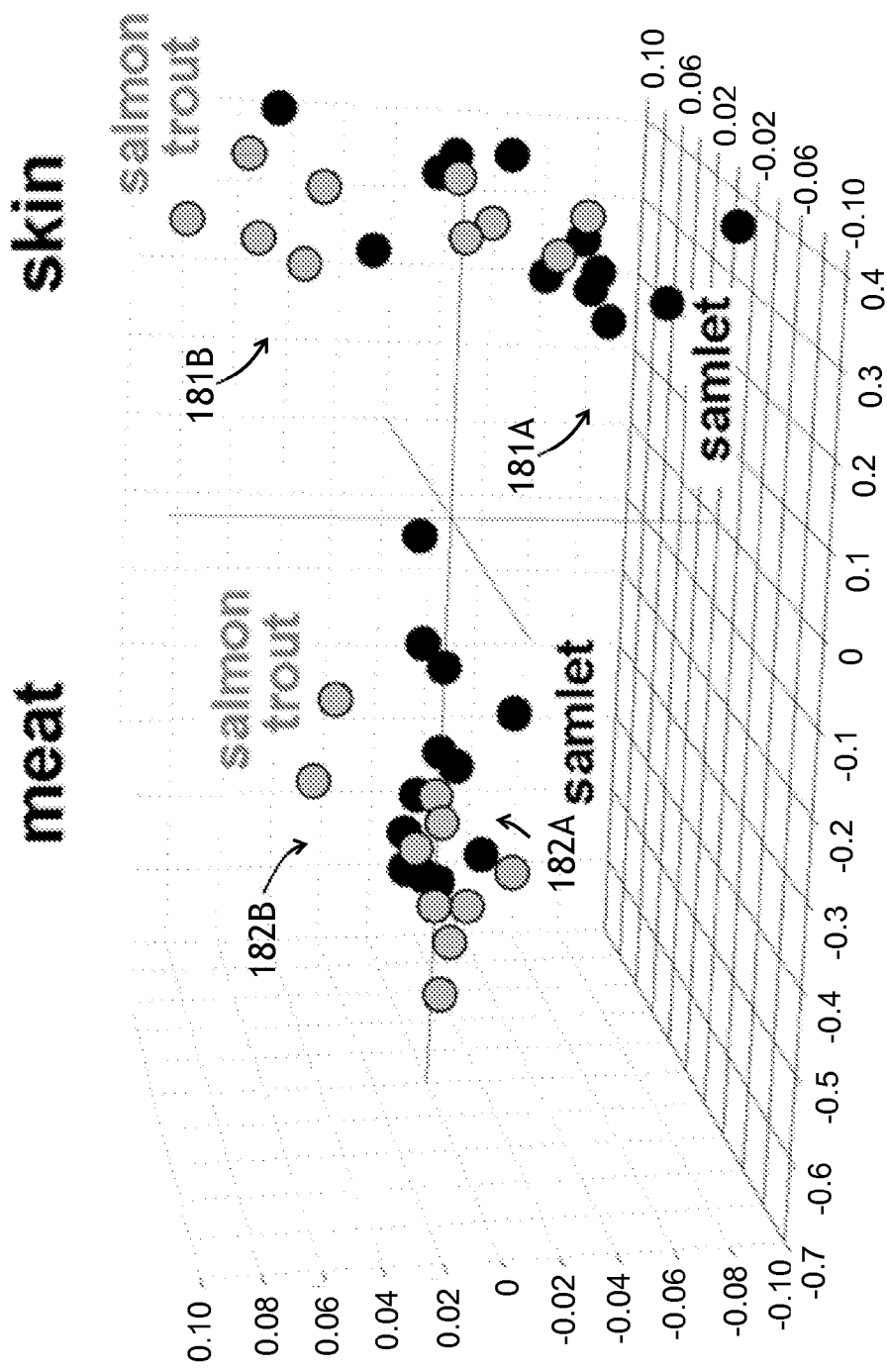

7); and samlet/salmon trout (skin and meat—FIG. 8), used in experimental verification of the invention;

FIG. 9 is a color photograph of a prototype of the apparatus measuring a NIR spectrum of a salmon sample;

FIGS. 10A and 10B are flow charts of data collection and analysis for higher and lower quality seafood, respectively, used in the experimental verification;

FIGS. 11, 14, and 17 are measured diffuse reflection spectra of the red mullet/mullet pair, winter codfish/codfish pair, and samlet/salmon trout pair, respectively;

FIGS. 12, 15, and 18 are three-dimensional score plots of principal component analysis (PCA) models of the red mullet/mullet pair, winter codfish/codfish pair, and samlet/salmon trout pair, respectively; and FIGS. 13A, B; 16A, B; and 19A, B are Coomans plots of Soft Independent Modeling of Class Analogy (SIMCA) analyses of the red mullet/mullet pair, winter codfish/codfish pair, and samlet/salmon trout pair, respectively.

DETAILED DESCRIPTION OF THE INVENTION

While the present teachings are described in conjunction with various embodiments and examples, it is not intended that the present teachings be limited to such embodiments. On the contrary, the present teachings encompass various alternatives and equivalents, as will be appreciated by those of skill in the art.

Figure 1:
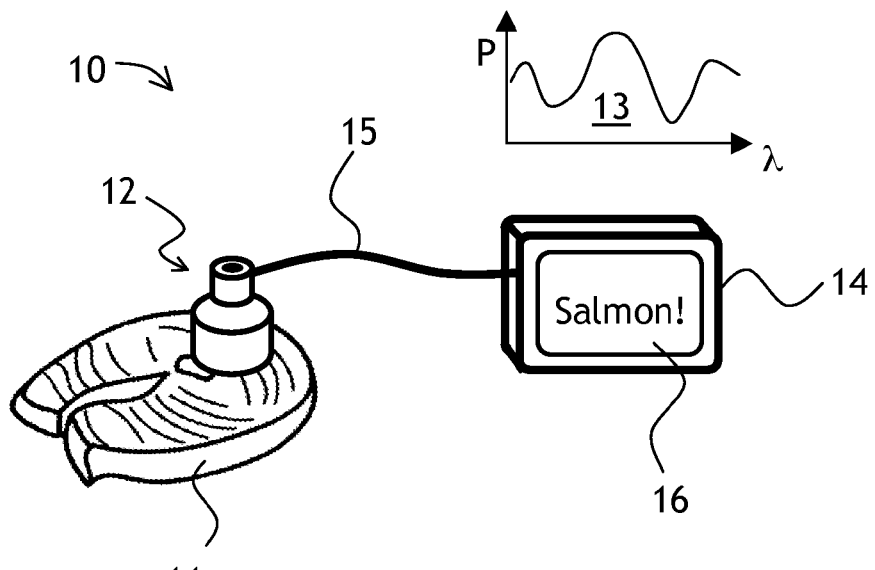
FIG. 1 is a schematic three-dimensional view of an apparatus for field authentication of a seafood sample according to the invention, superimposed with an NIR reflection spectrum measured by the apparatus.

Referring to FIG. 1, an apparatus 10 for field authentication of a seafood sample 11 includes a portable NIR spectrometer 12 for obtaining a diffuse NIR reflection spectrum 13 (signal power P vs. wavelength λ) of the seafood sample 11. An analyzer 14 is operationally coupled e.g. via a cable 15 to the spectrometer 12. The analyzer 14 is configured to perform a multivariate analysis of the reflection spectrum 13 of the seafood sample 11 to determine at least one characteristic parameter corresponding to the reflection spectrum 13. The analyzer 14 is configured for comparing the at least one parameter to a threshold corresponding to species of the seafood sample 11, for determination of the species of the seafood sample 11. The species can be displayed on a display 16 of the analyzer 14. The at least one parameter can include two or more parameters. The two parameters can be represented graphically as a point on an XY plot called Coomans plot. A position of the point on the Coomans plot is indicative of the seafood species of which the reflection spectrum 13 was taken. Multivariate regression/pattern recognition analysis and Coomans plots will be considered in detail further below. The construction of the NIR spectrometer 12 is considered first.

Figure 2:
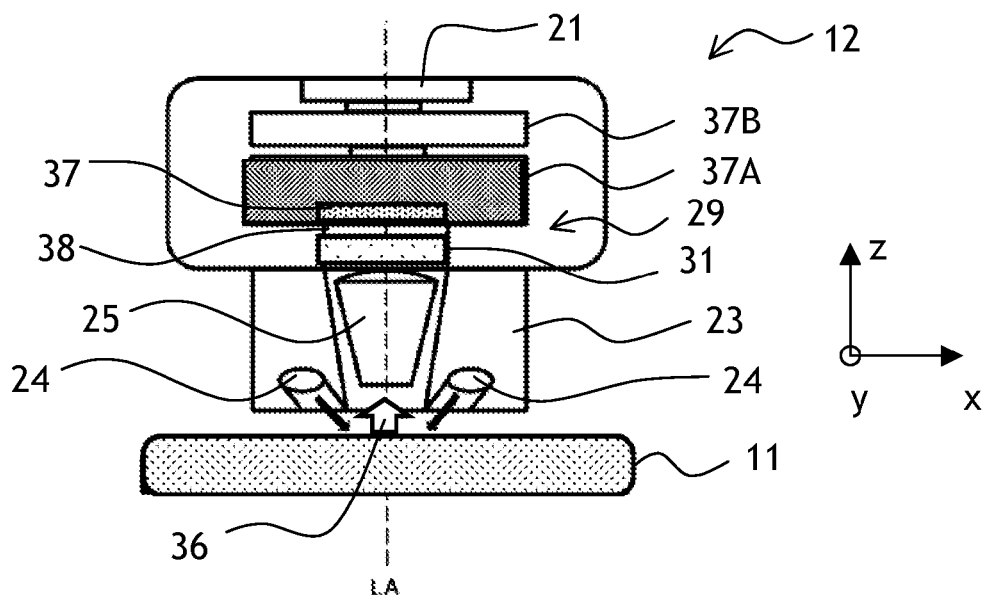
FIG. 2 is a side cross-sectional view of a portable handheld NIR spectrometer of the apparatus of FIG. 1.

Referring to FIG. 2, the NIR spectrometer 12 includes a body 23, incandescent lamps 24 for illuminating the seafood sample 11, a tapered light pipe (TLP) 25 for guiding diffusely reflected light 36, a laterally variable filter (LVF) 31 for separating the reflected light 36 into individual wavelengths, and a photodetector array 37 for detecting optical power levels of the individual wavelengths. The photodetector array 37 is formed in a CMOS processing chip 37A and coupled to the LVF 31 with a optically transmissive adhesive 38. An electronics board 37B is provided to support and control the CMOS processing chip 37A. An optional pushbutton 21 is provided to initiate the spectra collection. The photodetector array 37 is aligned perpendicular to a longitudinal axis LA of the TLP 25.

In operation, the incandescent lamps 24 illuminate the seafood sample 11. The TLP 25 collects the diffusely reflected light 36 and direct it towards the LVF 31. The LVF 31 separates the diffusely reflected light 36 into individual wavelengths, which are detected by the photodetector array 31. The measurement cycle can be initiated by pressing the pushbutton 21, or by an external command from the analyzer 14.

Figure 3A:
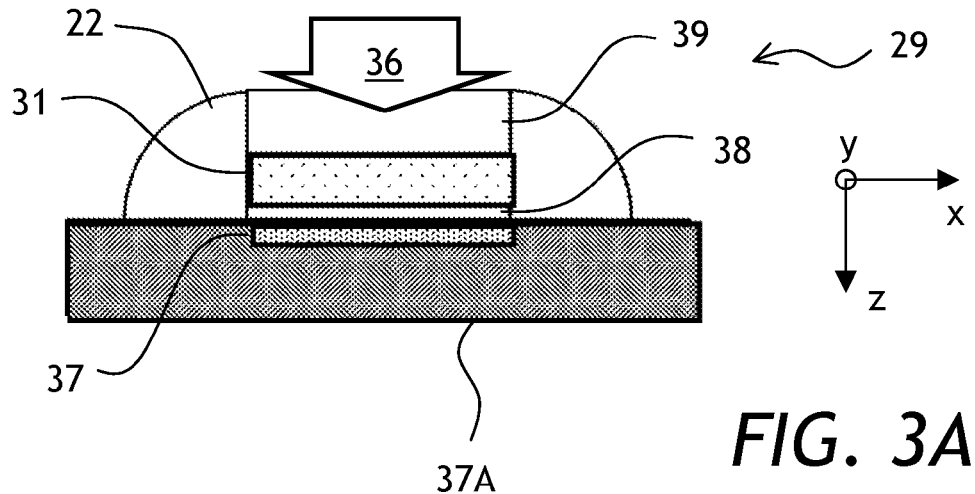
FIG. 3A is a side cross-sectional view of a light detection subassembly the portable NIR spectrometer of FIG. 2.

The compact size of the NIR spectrometer 12 is enabled by the construction of its light detection subassembly 29. Referring to FIG. 3A, the light detection subassembly 29 is shown in XZ plane. In FIG. 3A, the light detection subassembly 29 is flipped by 180 degrees as indicated by the direction of the z-axis on the right side of FIGS. 2 and 3A. In the preferred embodiment shown in FIG. 3A, the optically transparent adhesive 38 directly couples the photodetector array 37 to the LVF 31. The optically transparent adhesive 38 needs to: be electrically non-conductive or dielectric in nature; be mechanically neutral by achieving good adhesion strength with inducing stress or destructive forces to the detector array 37; optically compatible to transmit the desired spectral content; remove reflection created at air to glass interfaces; and have reasonable coefficient of thermal expansion properties to minimize stress to the detector pixels 52 during curing and during thermal cycling. Am opaque epoxy 22 encapsulates the LVF 31, facilitating removal of stray light and protecting the LVF 31 from humidity. An optional glass window 39 is placed on top of the LVF 31 for additional environmental protection.

Figure 3B:
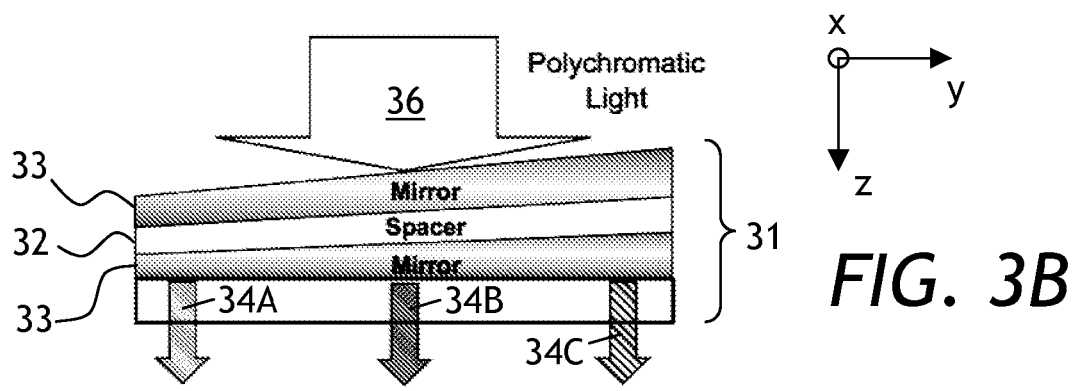
FIG. 3B is a side cross-sectional view of a wavelength dispersive element used in the light detection subassembly of FIG. 3A.
Figure 3C:
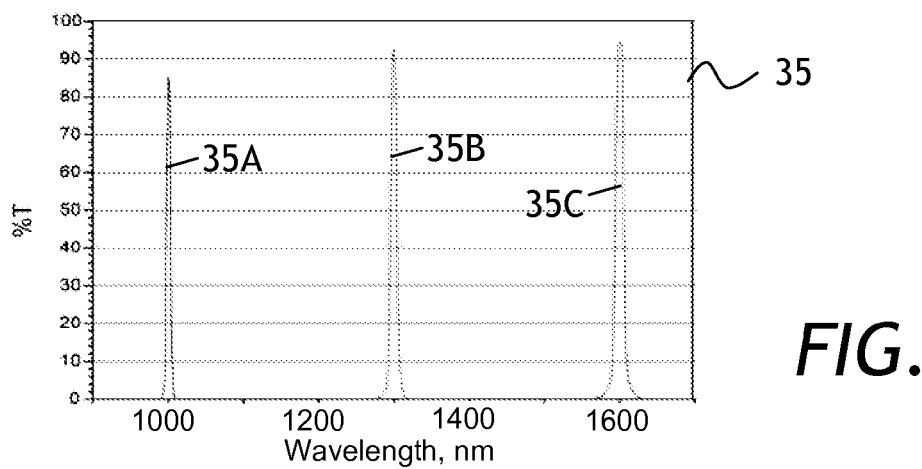
FIG. 3C is a transmission spectrum of the wavelength dispersive element of FIG. 3B.

Referring to FIGS. 3B, and 3C, the operation of the LVF 31 is illustrated. The LVF 31 is shown in YZ plane, in which the wavelengths are dispersed. The LVF 31 includes a wedged spacer 32 sandwiched between wedged dichroic mirrors 33, to form a Fabry-Perot interferometer with a laterally variable spacing between the dichroic mirrors 33. The wedge shape of the optical transmission filter 31 makes its transmission wavelength laterally variable, as shown with arrows 34A, 34B, and 34C pointing to individual transmission peaks 35A, 35B, and 35C, respectively, of a transmission spectrum 35 (FIG. 3C) shown under the variable optical transmission filter 31. In operation, the polychromatic light 36 reflected from the seafood sample 11 impinges on the variable optical filter 31, which separates the polychromatic light 36 into individual spectral components shown with the arrows 43A to 34C. The wavelength range of the NIR spectrometer 12 is preferably between 700 nm and 2500 nm, and more preferably between 950 nm and 1950 nm.

Figure 3D:
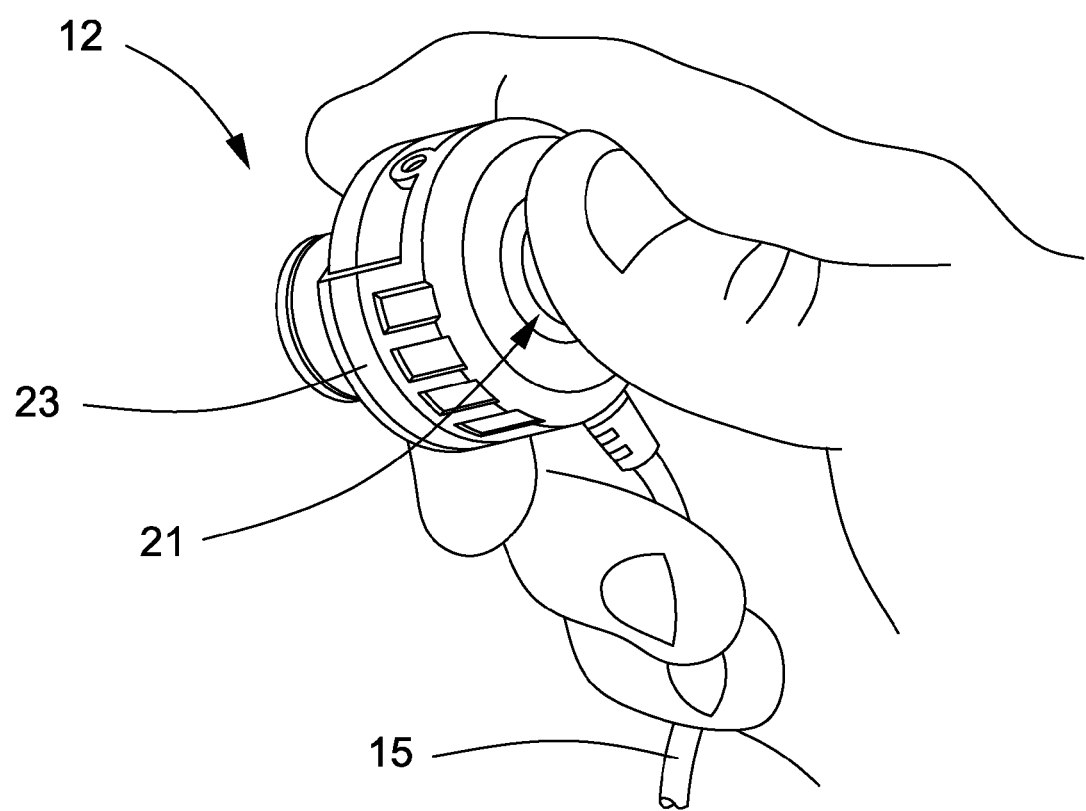
FIG. 3D is a three-dimensional view of the portable handheld NIR spectrometer of FIG. 2.

Using the LVF 31 and the TLP 25 allows a considerable size reduction of the NIR spectrometer 12. The NIR spectrometer 12 is free of any moving parts for wavelength scanning Small weight of the NIR spectrometer 12, typically less than 100 g, allows a direct placement of the NIR spectrometer 12 onto the seafood sample 11. Small weight and size also makes the NIR spectrometer 12 easily transportable e.g. in a pocket of a food inspector. The size of the NIR spectrometer 12 is illustrated in FIG. 3D. The NIR spectrometer 12 can easily be held in hand, with the pushbutton 21 conveniently located for thumb operation.

Many variants of the NIR spectrometer are of course possible. For instance, the incandescent bulbs 24 can be replaced with broadband light emitting diodes or LEDs. The TLP 25 can be replaced with another optical element, such as a fiber optic plate or a holographic beam shaper. The LVF 31 can be replaced with another suitable wavelength-selective element such as a miniature diffraction grating, an array of dichroic mirrors, a MEMS device, etc.

Figure 4A:
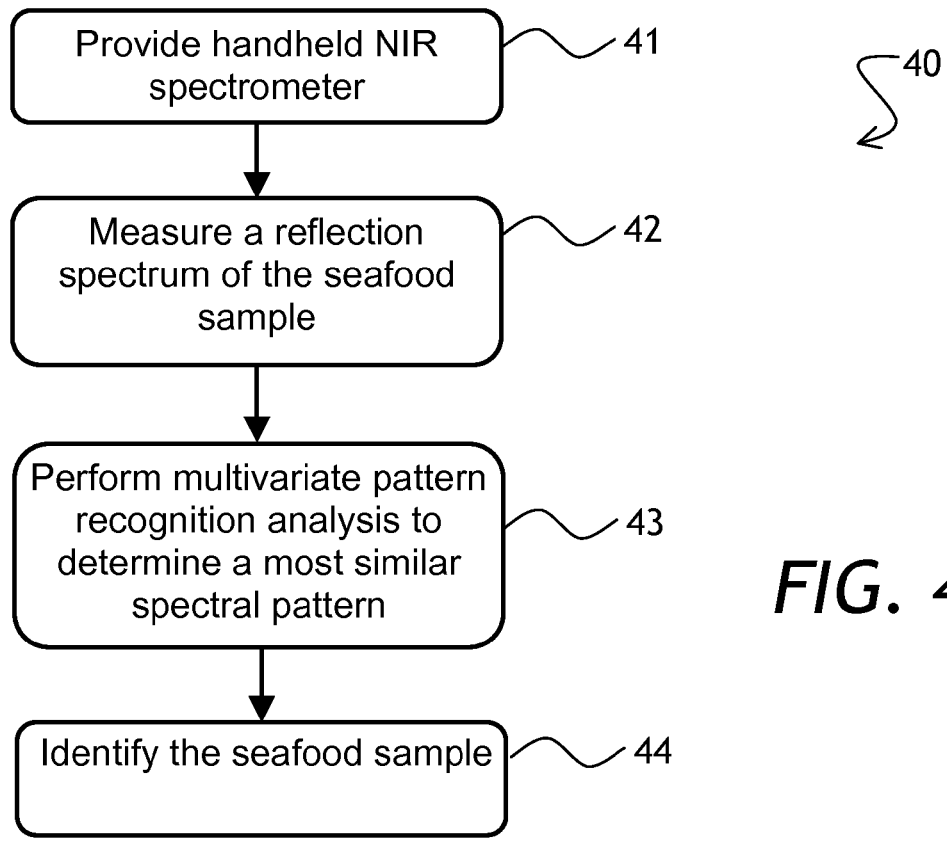
FIG. 4A is a flow chart of a method for field authentication of a seafood sample according to the invention.

Referring to FIG. 4A with further reference to FIG. 1, a method 40 for field authentication of the seafood sample 11 includes a step 41 of providing the portable NIR spectrometer 12 described above. In a step 42, the reflection spectrum 13 of the seafood sample 11 is obtained using the NIR spectrometer 12. In a step 43, a multivariate pattern recognition analysis of the reflection spectrum 13 of the seafood sample 11 is performed to determine a matching spectrum with a most similar spectral pattern by comparing the reflection spectrum 13 to a library of known identity spectra corresponding to different species of seafood. Finally, in a step 44, the seafood sample 11 is identified based on the matching spectrum bearing the most similar spectral pattern determined in the previous step 43.

Herein, the term "matching spectrum" does not of course denote an exact match. Instead, it denotes an identity spectrum of the library, carrying the most similar spectral pattern, as compared to the measured reflection spectrum 13. Thus, the "match" does not have to be exact, only the closest match of those available. The proximity of the match can be calculated based on the particular matching evaluation method used.

The multivariate pattern recognition analysis 43 is performed to extract seafood species information from the reflection spectrum 13. Due to multitude of overtones of vibrational frequencies of characteristic molecular bonds, the reflection spectrum 13 can be very complex, so that individual spectral peaks cannot be visually identified. According to the invention, the multivariate pattern recognition analysis 43, also known as "chemometric analysis", is performed to identify or authenticate species of the seafood sample 11.

The measuring step 42 preferably includes performing repetitive spectral measurements at different locations on the seafood sample 11, and averaging the repetitive measurements, to lessen a dependence of the obtained reflection spectrum on a texture of the seafood sample 11. Extended Multiplicative Scatter Correction (EMSC) of the reflection spectrum 13 can be used to reduce dependence of the measured reflection spectrum 13 on scattering properties of the seafood sample 11.

The reflection spectrum 13 can also be pre-processed using other known statistical methods, e.g. a Standard Normal Variation (SNV) of the reflection spectrum 13 can be computed before proceeding to the multivariate pattern recognition analysis step 43. The slope and/or inflection of the spectral features in the reflection spectrum 13 can be accounted for by performing Savitzky-Golay filtering of the reflection spectrum 13, and computing a first and/or second derivative of the reflection spectrum 13 to be accounted for in the multivariate pattern recognition analysis step 43. Other statistical methods, such as sample-wise normalization and/or channel-wise auto-scaling of the reflection spectrum 13, can be used to facilitate the multivariate pattern recognition analysis step 43, and to provide more stable results.

The multivariate pattern recognition analysis 43 is usually performed in two stages. By way of example, referring to FIG. 4B with further reference to FIG. 1, a PCA step 45 is performed at first, to define a calibration model for each seafood type that needs to be identified. The PCA step 45 can be done in advance, before measuring the seafood sample 11, at a calibration stage of the apparatus 10. In a second step 46, similarities between the collected reflection spectrum 13 and the calibration models of different seafood species are analyzed. In the embodiment shown, soft independent modeling of class analogies (SIMCA) is used. As a result of the SIMCA step 46, two parameters are determined. These two parameters are plotted in a XY plot (Coomans plot), different areas of which correspond to different seafood species. Only one parameter is required in some cases, and this parameter can be compared to a threshold determined in the PCA step 45, to authenticate the seafood sample 11. Other multivariate pattern recognition analysis methods can be applied. Examples of these methods are considered below in the "Experimental Verification" section.

Figure 4B:
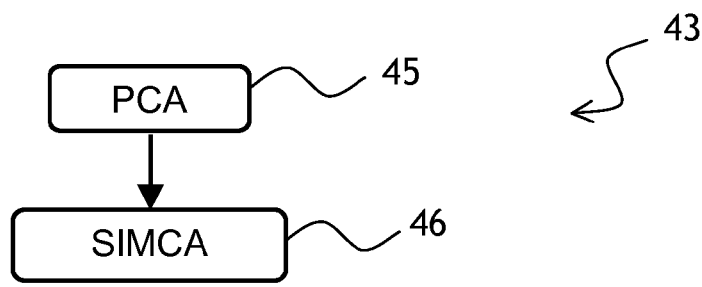
FIG. 4B is a flow chart of an exemplary multivariate analysis of the NIR spectra according to the invention.
Figure 5A:
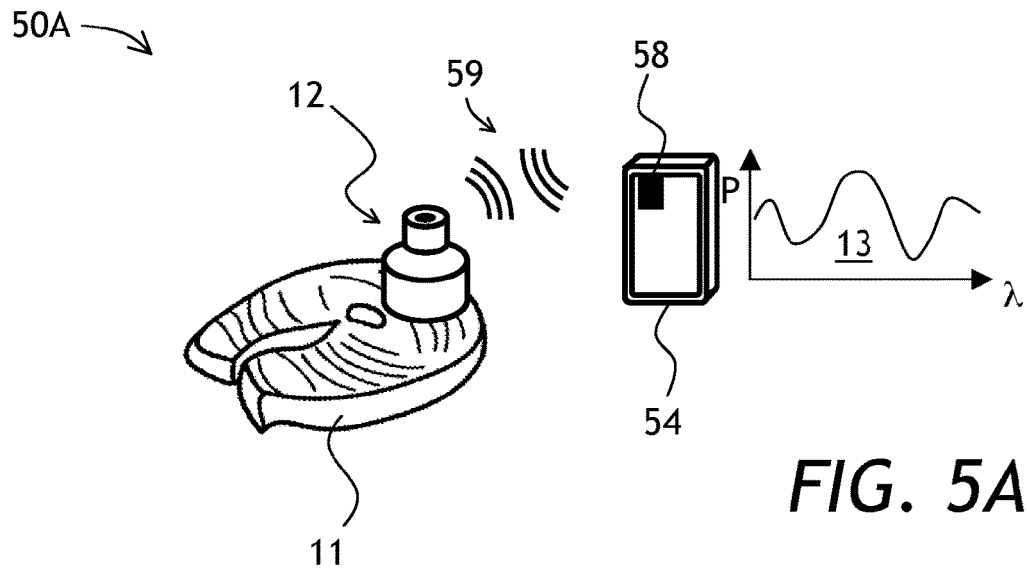
FIG. 5A is a schematic view of one embodiment of the apparatus of the invention, in which a portable device in wireless communication with the NIR spectrometer is used to analyze NIR spectra obtained by the NIR spectrometer.

In view of proliferation of computerized mobile communication devices such as smartphones, it is advantageous to use a mobile communication device to perform the multivariate pattern recognition analysis step 43 (FIGS. 4A and 4B). Referring to FIG. 5A with further reference to FIGS. 1 and 4A, an apparatus 50A for field authentication of the seafood sample 11 is similar to the apparatus 10 of FIG. 1. One difference is that in the apparatus 50A of FIG. 5A, a mobile communication device 54 is configured to perform the multivariate analysis step 43 and the identification step 44 of the method 40 of FIG. 4A. To that end, the mobile communication device 54 can include a non-transitory storage medium 58 having encoded thereon the library of the known identity spectra corresponding to different species of seafood, and/or computer instructions for performing the multivariate pattern recognition/data reduction analysis step 43. The mobile communication device 54 can be coupled to the NIR spectrometer 12 via a wireless link 59 such as Bluetooth™, or via a wired e.g. USB communication, for communicating the obtained reflection spectrum 13 to the mobile communication device 54.

Figure 5B:
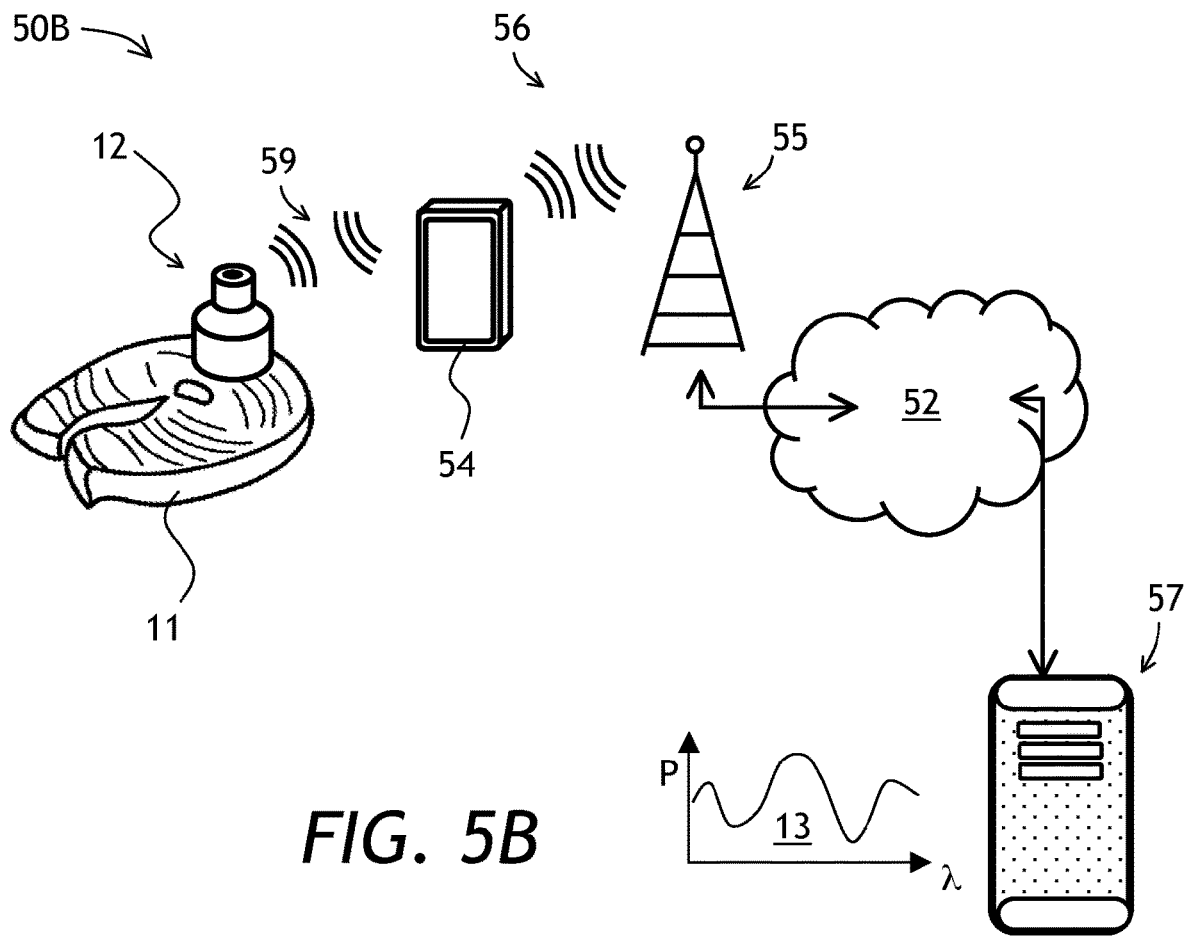
FIG. 5B is a schematic view of another embodiment of the apparatus of the invention, in which the portable device is used to relay the measured NIR spectra to a remote server for performing the multivariate analysis.

Turning now to FIG. 5B with further reference to FIGS. 4A and 5A, an apparatus 50B for field authentication of a seafood sample is similar to the apparatus 50A of FIG. 5A. The apparatus 50B of FIG. 5B includes a remote server 57 in communication with the mobile communication device 54 via an RF communication link 56 to a cell tower 55 connected to the Internet 52. In operation, the reflection spectrum 13 is communicated from the mobile device 54 to the remote server 57, and the multivariate pattern recognition analysis, i.e. the step 43 of the method 40 of FIG. 4A, is performed at the remote server 57. The result of the multivariate analysis step 43 (FIG. 4A) is communicated back to the mobile device 54 (FIG. 5B) for displaying to a user, not shown. The identification step 44 (FIG. 4A) can be performed either by the mobile device 54 or by the remote server 57 (FIG. 5B). Using the computational power of a remote server frees up the resources on the mobile communication device, and as a result can speed up the overall process of seafood identification.

Experimental Verification

Figure 6:
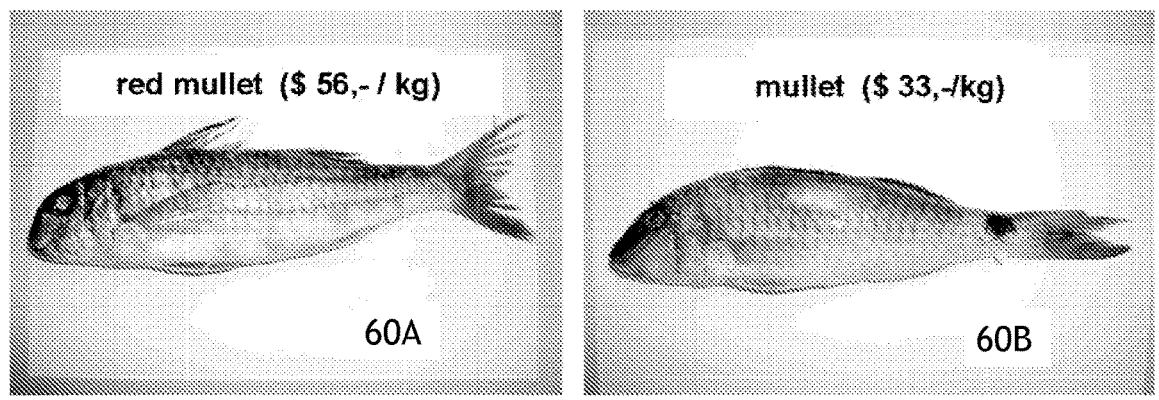
FIGS. 6 to 8 are color photographs of seafood pairs to be discriminated between, including: red mullet/mullet pair (FIG. 6); winter codfish/codfish pair (skin and meat—FIG.
Figure 7:
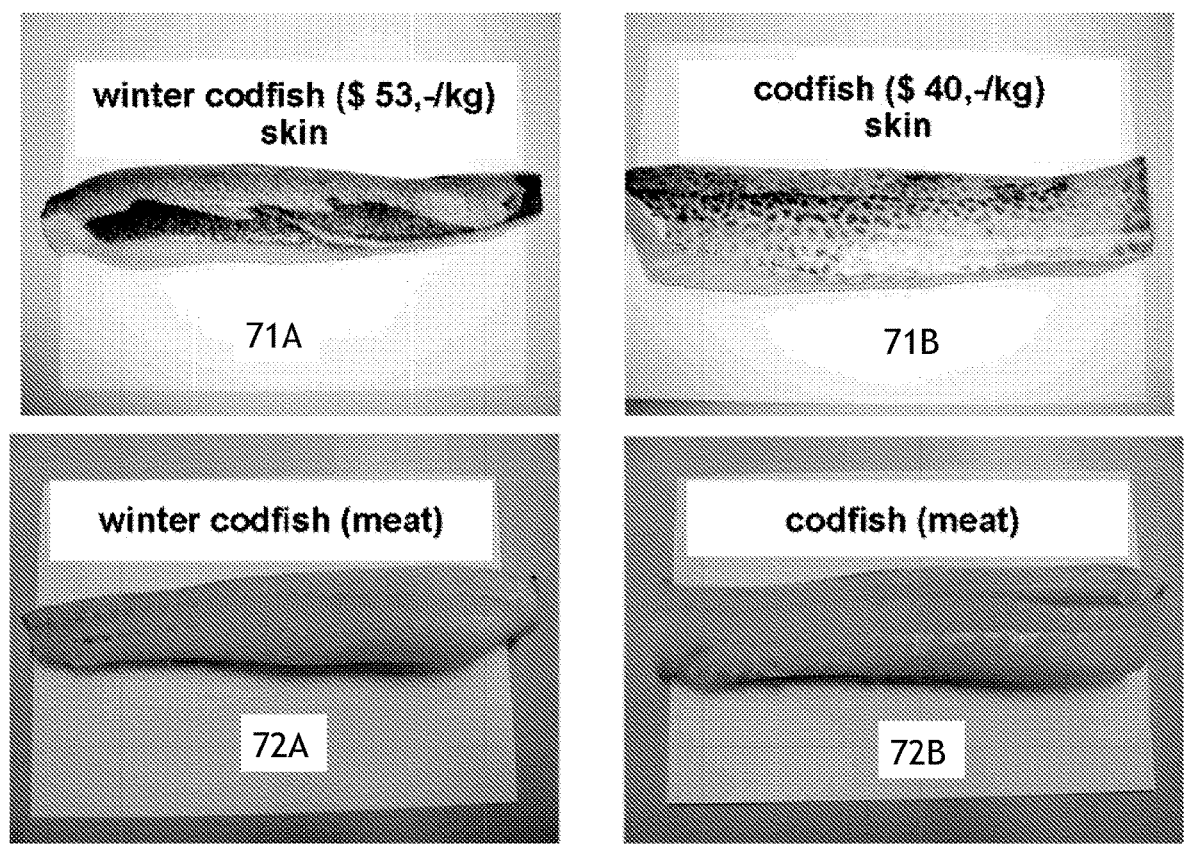
Figure 8:
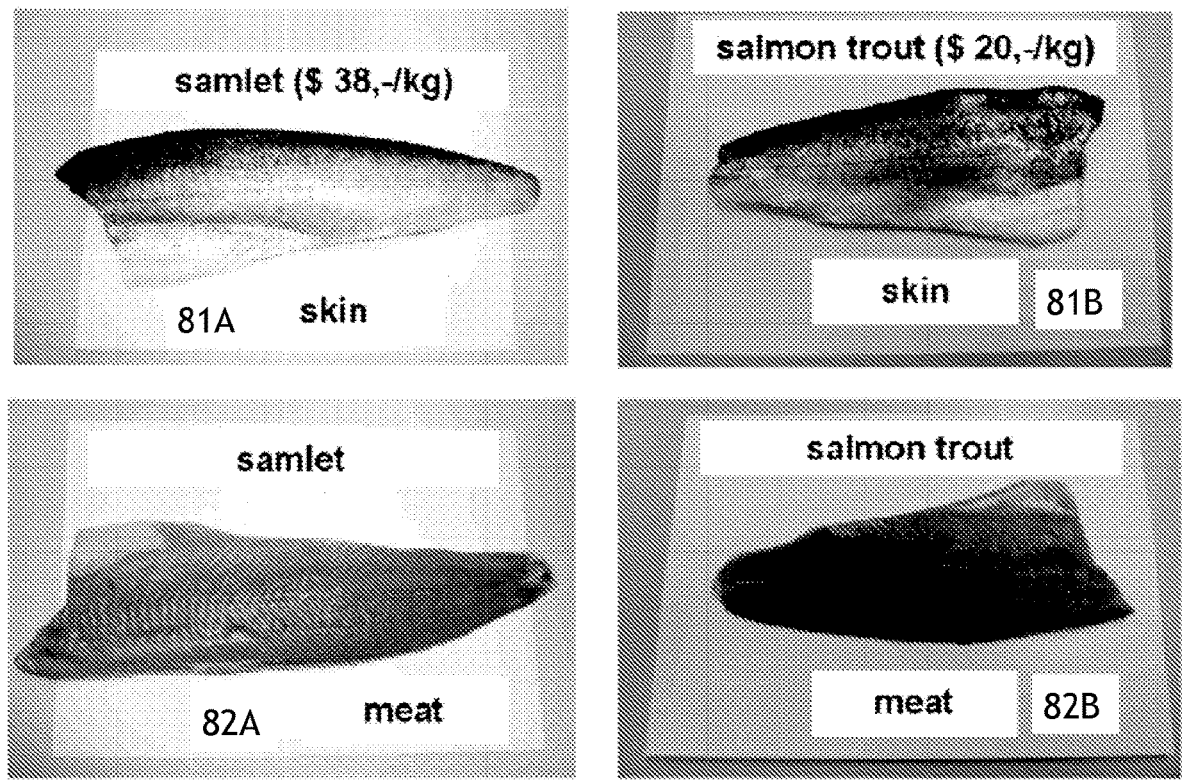

A number of experiments were performed to verify that similarly looking, but differently priced fish species can be identified using a combination of NIR spectroscopy and multivariate regression (chemometric) analysis. Referring to FIGS. 6 to 8, three sets of different fish species were used. The first set included a whole red mullet 60A and a whole mullet 60B (FIG. 6), both skin and meat (the meat is not shown). The second set included: winter codfish skin 71A; codfish skin 71B; winter codfish meat 72A; and codfish meat 72B. The third set included: samlet skin 81A; salmon trout skin 81B; samlet meat 82A; and salmon trout meat 82B. As can be seen from the photos of FIGS. 6 to 8, even for a seafood professional such as a merchant or a cook, let alone a general public customer, the visual discrimination of the whole fish and the fish filets would be rather challenging. In FIGS. 6 to 8, the "A" group includes more expensive species 60A, 71A, 72A, 81A, and 82A, and the "B" group includes less expensive species 60B, 71B, 72B, 81B, and 82B. Thus, substitution of "A" species with "B" species can provide a substantial economic benefit.

Turning to FIG. 9, an apparatus 90 used in the experimental verification of the invention included MicroNIR™ 1700 spectrometer 92 manufactured by JDS Uniphase Corporation, Milpitas, Calif., USA. The MicroNIR spectrometer 92 was operated in a wavelength range of 950 nm to 1650 nm. The MicroNIR spectrometer 92 is a low-cost, ultra-compact portable spectrometer that weighs 60 grams and is less than 50 mm in diameter. The spectrometer 92 operates in a diffuse reflection and is constructed similarly to the spectrometer 12 of FIG. 3B, including a light source (not shown) for illuminating the seafood sample 11, the dispersing element 31, the photodetector array 37, and electronics (not shown), which are all contained in a small portable package that can be placed directly on a seafood sample 91. The spectrometer 92 is connected by a cable 95 to a laptop computer 94 running Unscrambler™ multivariate analysis software provided by CAMO AS, Oslo, Norway (version 9.6). For each spectral measurement, 50 scans having integration times of 5 milliseconds have been accumulated, resulting in a total measurement time of 0.25 seconds per reflection spectrum measurement.

Referring now to FIGS. 10A and 10B, flow charts 100A and 100B represent spectra acquisition and PCA model building steps performed for the fish samples 60A and 60B; 71A and 71B; 72A and 72B; 81A and 81B; and 82A and 82B, respectively. In steps 101A and 101B, three different individual pieces were provided for each fish sample 60A and 60B; 71A and 71B; 72A and 72B; 81A and 81B; 82A and 82B, respectively, of FIGS. 6 to 8. For mullets 60A and 60B; winter codfish/codfish 71A and 71B; 72A and 72B, and samlet/salmon trout 81A and 81B; 82A and 82B pairs, the skin reflection spectra were collected in steps 102A and 102B, respectively; and the meat reflection spectra were collected in steps 103A and 103B, respectively. A total of ten NIR reflection spectra were obtained at different positions on each of the three pieces, resulting in thirty measurements for each fish sample 60A; 60B; 71A; 71B; 72A; 72B; 81A; 81B; 82A; and 82B of FIGS. 6 to 8. The spectra were corrected for scattering using a standard method of extended multiplicative scatter correction.

Thus, the total of thirty spectra have been obtained for each fish skin type 60A and 60B; 71A and 71B; 81A and 81B in steps 104A and 104B, respectively. The total of thirty spectra have been obtained for each fish meat type 72A and 72B; 82A and 82B in steps 105A and 105B, respectively. The spectra have been averaged in groups of five for each of the three samples of each type in respective steps 106A, 107A; and 106B, 107B, resulting in two averaged spectra for each sample, and six averaged spectra for each sample type, including skin and meat. The averaging was done to lessen a dependence of the obtained reflection spectrum on a texture of respective the seafood samples 60A; 60B; 71A; 71B; 72A; 72B; 81A; 81B; 82A; and 82B. Then, PCA models have been established in steps 108A, 108B for the respective "A" and "B" samples. A SIMCA analysis was performed to identify the type of each fish sample. The results were presented in form of Coomans plots for each fish type.

Red Mullet/Mullet Pair

Referring to FIG. 11 with further reference to FIG. 6, reflection spectra of the red mullet 60A and mullet 60B are shown as dependence of reflection signal in arbitrary units on the wavenumber in inverse centimeters (cm$^{-1}$), in the range between 10900 to 6000 cm$^{-1}$. Twelve traces including six spectra of red mullet skin and the six spectra of mullet skin are shown at 111. Twelve traces including the respective six spectra of red mullet meat and six spectra of mullet meat are shown at 112. One can see that the spectra 111 of red mullet and mullet skin are quite similar to each other, and the spectra 112 of red mullet and mullet meat are quite similar to each other as well, so visually the spectra of red mullets cannot be differentiated from the spectra of mullets, for both skin and meat.

Turning to FIG. 12 with further reference to FIGS. 10A and 10B, the results of the PCA analysis steps 108A, 108B (FIG. 10B) are presented. In FIG. 12, red mullet skin score points 121A are sufficiently separated from mullet skin score points 121B to allow easy identification, but no clear separation was achieved between red mullet meat score points 122A and mullet meat score points 122B.

Figure 13B:
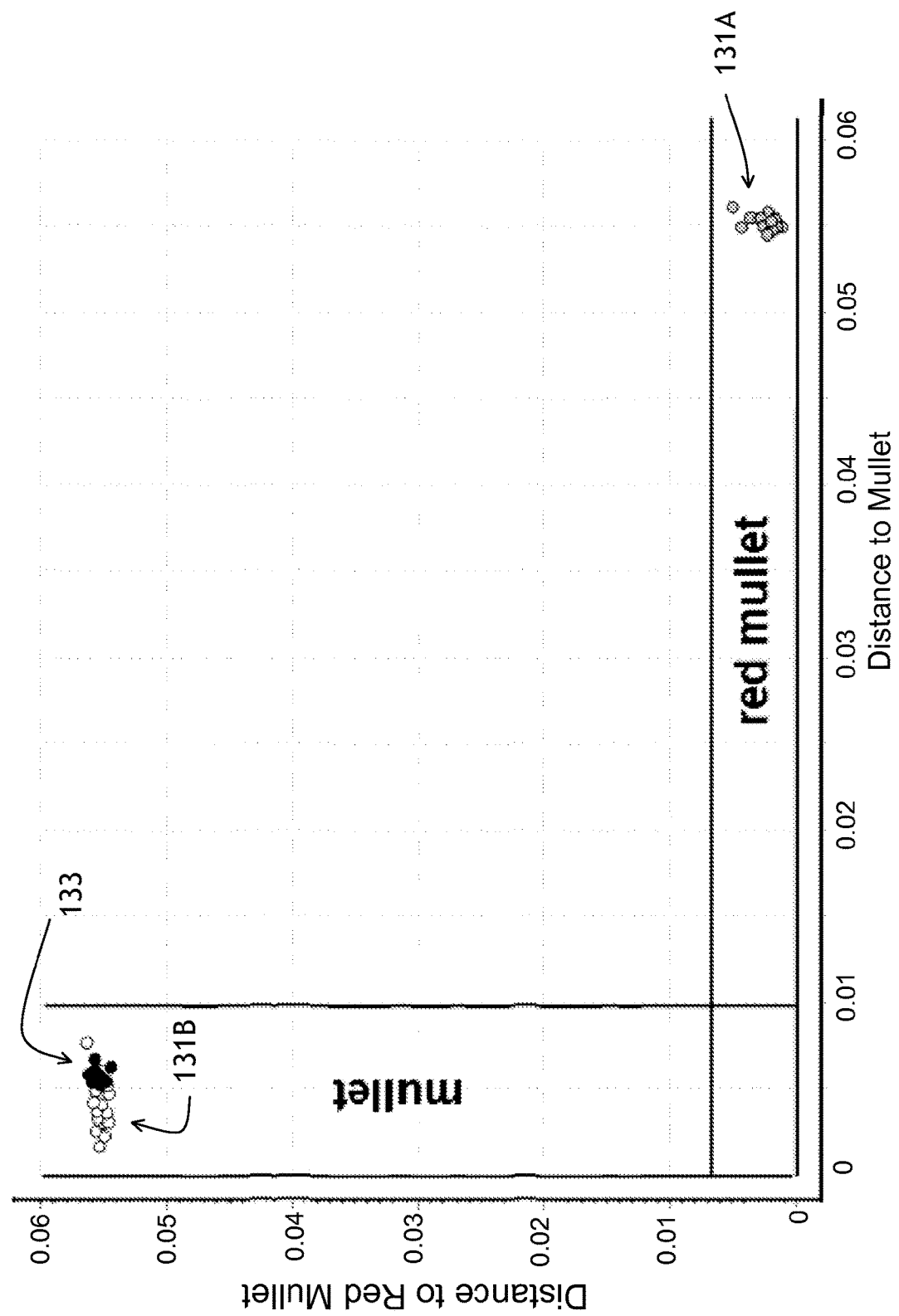

Referring now to FIGS. 13A and 13B, results of SIMCA analysis of red mullet/mullet pair are presented in form of Coomans plots at 5% significance. FIG. 13A shows results of red mullet sample identification. Gray-colored circles 131A represent calibration red mullet samples, skin and meat, used to obtain the identity spectra of red mullet; white-filled circles 131B represent calibration mullet samples, skin and meat, used to obtain the identity spectra of mullet; and filled (black) circles 132 represent the test sample. The total of four black circles correspond to one red mullet skin sample and one red mullet meat samples, each represented by two averaged spectra. FIG. 13B shows results of mullet sample identification. Filled (black) circles 133 represent two test samples. The total of eight black circles 133 correspond to two mullet skin samples and two mullet meat samples, each represented by two averaged spectra as explained above.

Only one of the two parameters "Distance to Red Mullet" and "Distance to Mullet" can be used by comparing the parameter to a threshold. For example, if "Distance to Mullet" is used, the threshold is about 0.01. If "Distance to Red Mullet" is used, the threshold is approximately 0.0008. One can see from FIGS. 13A and 13B that red mullet, both skin and meat, are both readily identifiable. Thus, removing skin of the fish sample would not allow a potential wrongdoer to hide an illegal act of substituting red mullet with mullet.

Winter Cod/Cod Pair

Referring to FIG. 14 with further reference to FIG. 7, reflection spectra of the winter cod skin 71A, winter cod meat 72A, cod skin 71B, and cod meat 72B (FIG. 7) are shown as dependence of reflection signal in arbitrary units on the wavenumber in inverse centimeters (cm$^{-1}$), in the range between 10900 to 6000 cm$^{-1}$. Twelve traces including the six spectra of winter cod skin and the six spectra of cod skin are shown at 141. Twelve traces including the respective six spectra of winter cod meat and six spectra of cod meat are shown at 142. One can see that the spectra 141 of winter cod and cod skin are quite similar to each other, and the spectra of winter cod and cod meat are also very similar, so visually the spectra of winter cod cannot be differentiated from the spectra of cod, for both skin and meat samples.

Turning to FIG. 15 with further reference to FIGS. 10A and 10B, the results of the PCA analysis steps 108A, 108B (FIG. 10B) are presented. In FIG. 15, winter cod skin score points 151A appear interspersed with cod skin score points 151B, and winter cod meat score points 152A appear interspersed with cod meat score points 152B, so no clear distinction can be made at this stage.

Figure 16A:
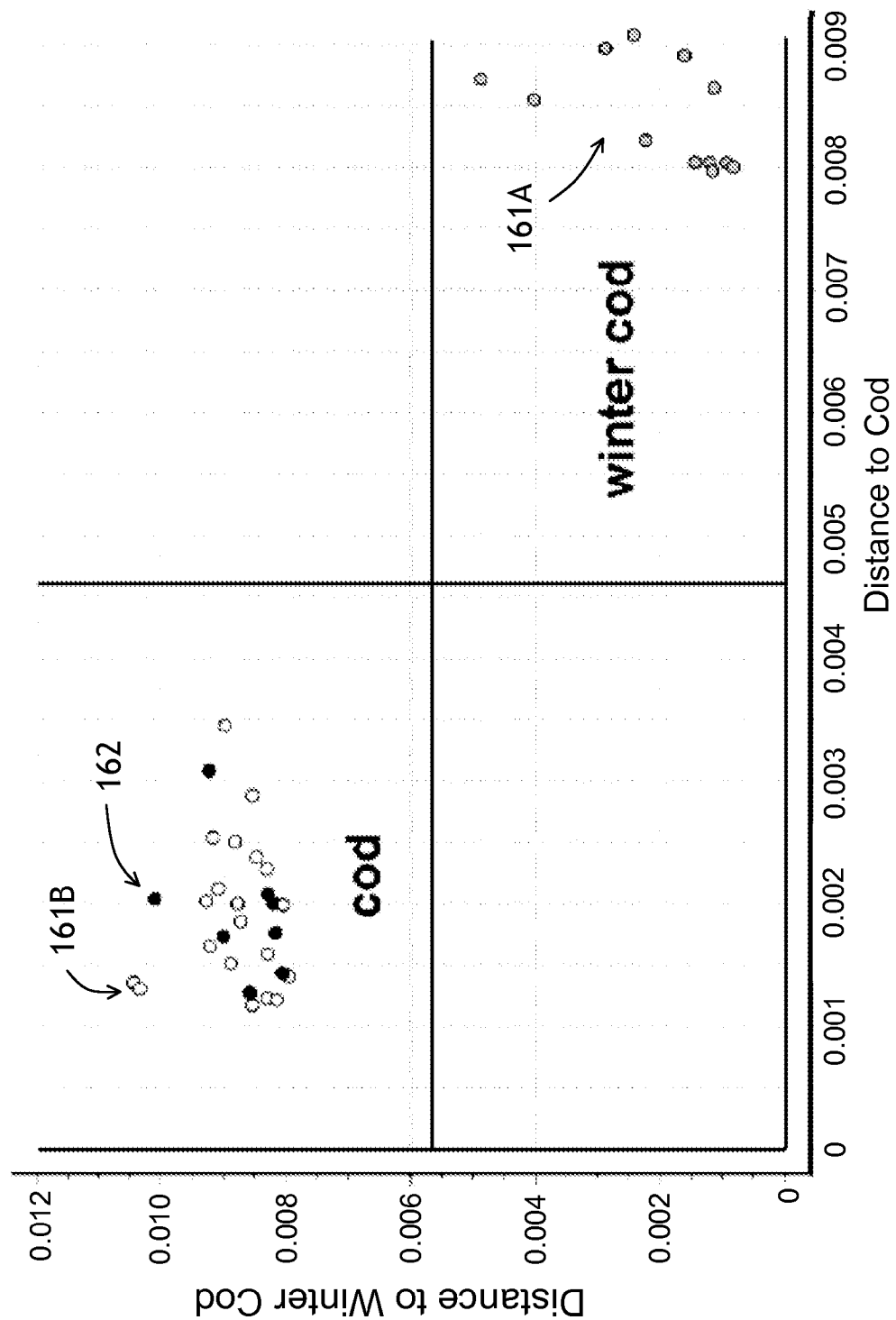
Figure 16B:
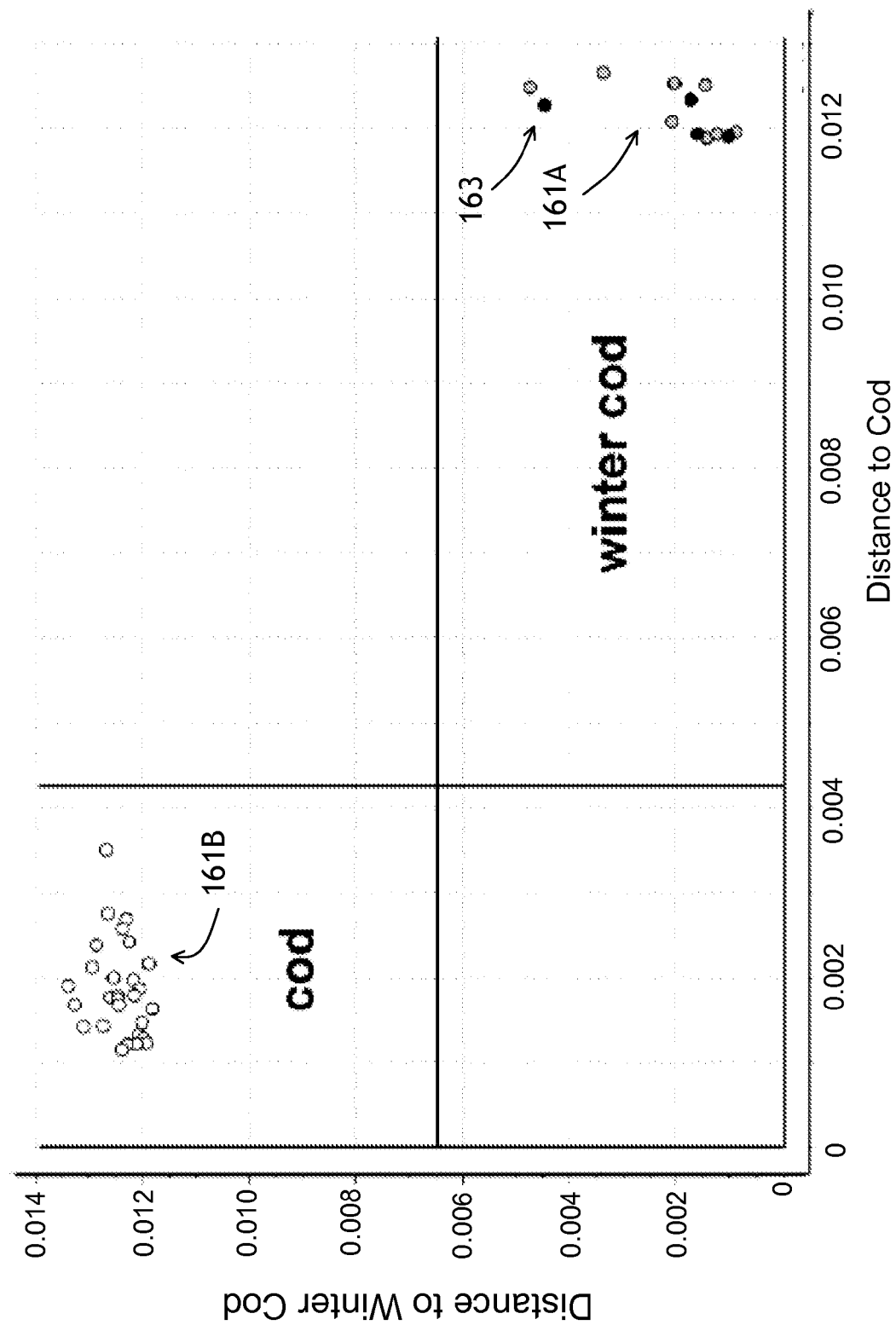

Referring now to FIGS. 16A and 16B, results of SIMCA analysis of winter cod/cod pair are presented in form of Coomans plots at 5% significance. FIG. 16A shows results of cod sample identification. Gray-colored circles 161A represent calibration winter cod samples, both skin and meat, used to obtain the identity spectra of winter cod; white-filled circles 161B represent calibration cod samples, both skin and meat, used to obtain the identity spectra of cod; and filled (black) circles 162 represent the test sample. The total of eight black circles correspond to two cod skin samples and two cod meat samples, each represented by two averaged spectra as explained above. FIG. 16B shows results of winter cod sample identification. Filled (black) circles 163 represent one test sample. The total of four black circles 163 correspond to one winter cod skin sample and one winter cod meat sample, each represented by two averaged spectra. One can see from FIGS. 16A and 16B that winter cod, both skin and meat, is readily identifiable and distinguishable from cod.

Samlet/Salmon Pair

Referring to FIG. 17 with further reference to FIG. 8, reflection spectra of the samlet skin 81A, samlet meat 82A, salmon trout skin 81B, and salmon trout meat 82B are shown as dependence of reflection signal in arbitrary units on the wavenumber in inverse centimeters ($cm^{-1}$), in the range between 10900 to 6000 $cm^{-1}$. Twelve traces including the six spectra of samlet skin and the six spectra of salmon trout skin are shown at 171. Twelve traces including the respective six spectra of samlet meat and six spectra of salmon trout meat are shown at 172. One can see that the skin spectra 171 of samlet and salmon trout are quite similar to each other, and the meat spectra 172 of samlet and salmon trout are also very similar, so visually the spectra of samlet cannot be differentiated from the spectra of salmon trout, for both skin and meat samples.

Turning to FIG. 18 with further reference to FIGS. 10A and 10B, the results of the PCA analysis steps 108A, 108B (FIG. 10B) are presented. In FIG. 18, samlet skin score points 181A appear interspersed with salmon trout skin score points 181B, and samlet meat score points 182A appear interspersed with salmon trout meat score points 182B, so that no clear distinction can be made at this stage.

Figure 19A:
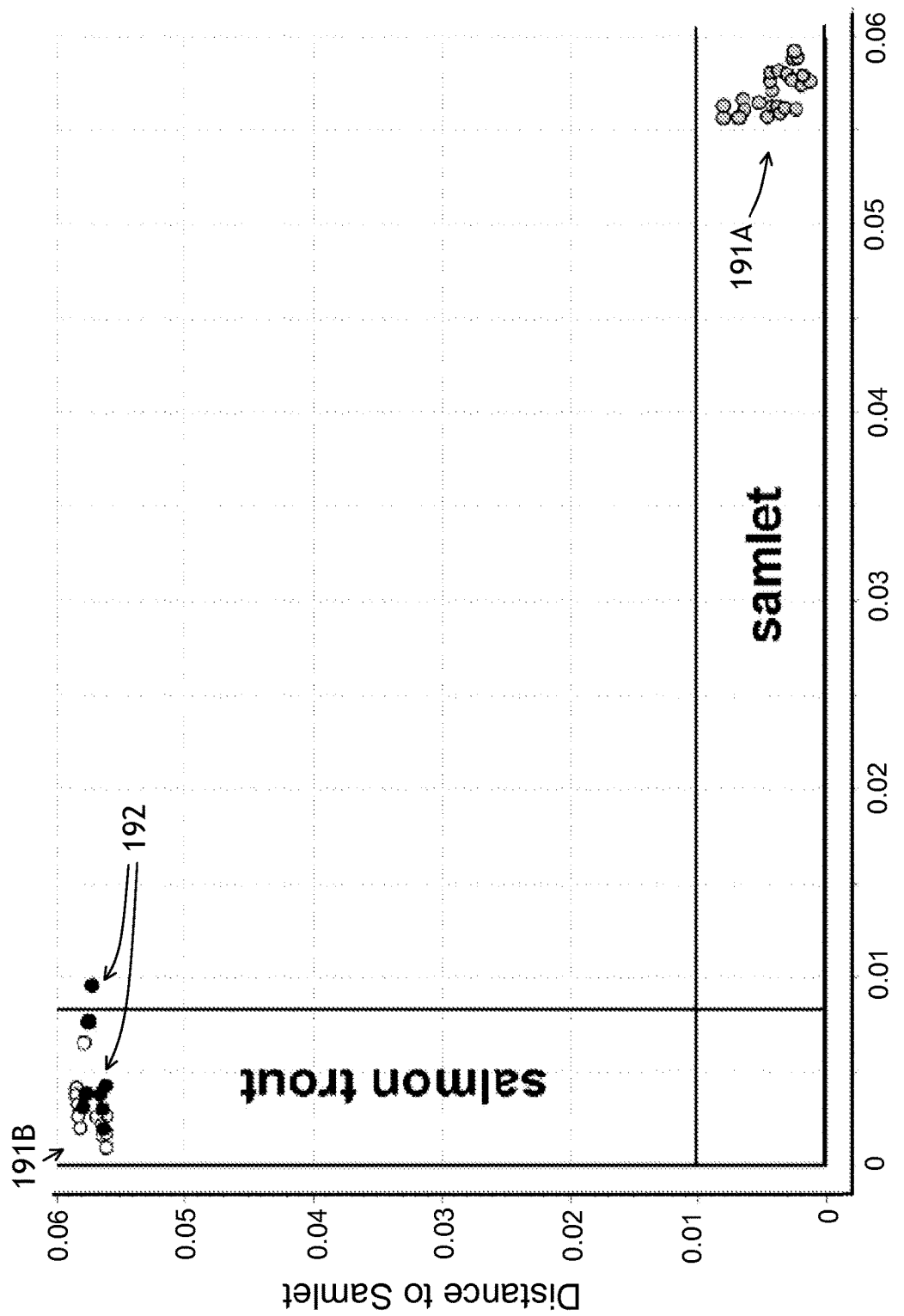
Figure 19B:
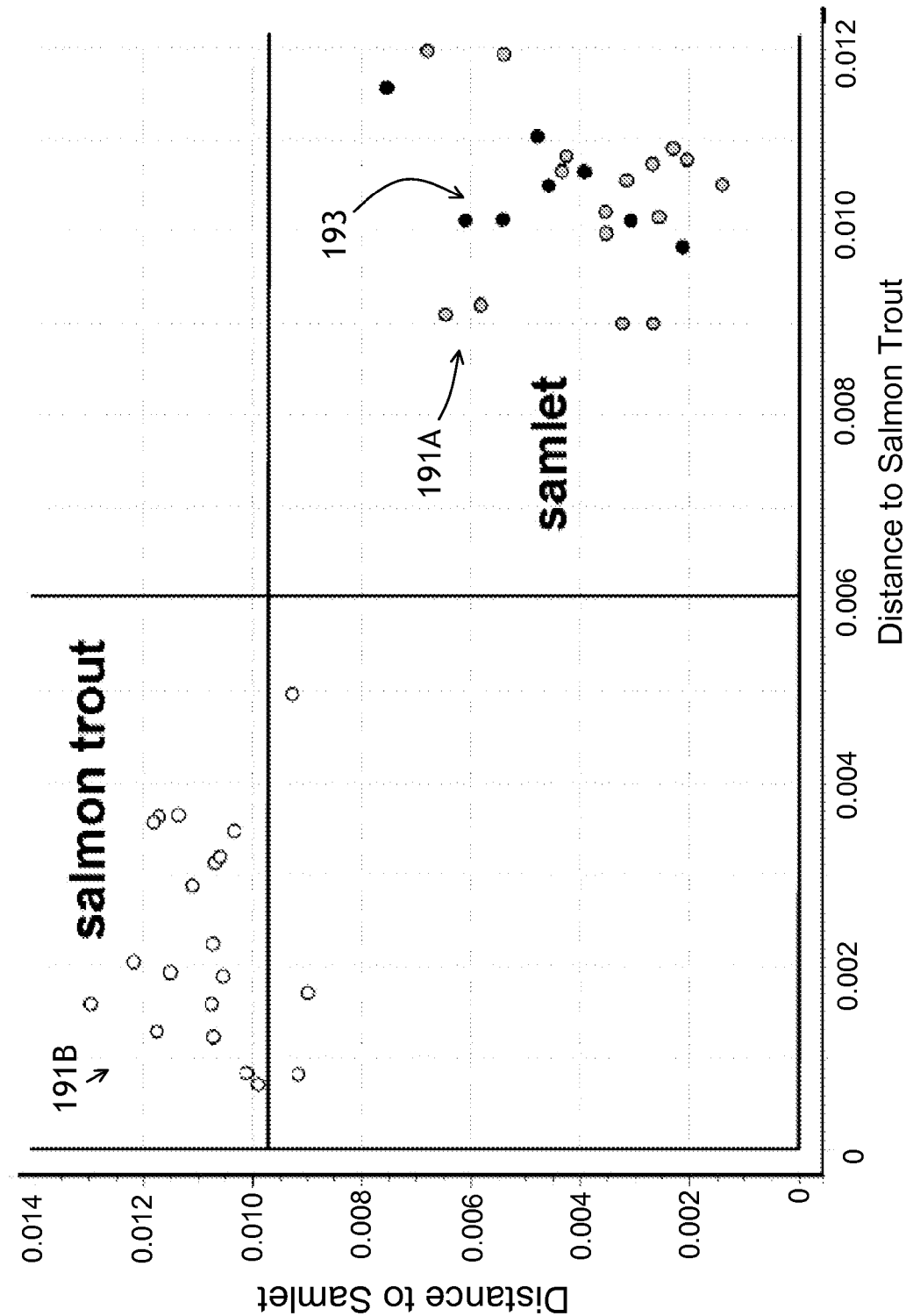

Referring now to FIGS. 19A and 19B, results of SIMCA analysis of samlet/salmon trout are presented in form of Coomans plots at 5% significance. FIG. 19A shows results of salmon trout sample identification. Gray-colored circles 191A represent calibration samlet samples, both skin and meat, used to obtain the identity spectra of samlet; white-filled circles 191B represent calibration salmon trout samples, both skin and meat, used to obtain the identity spectra of salmon trout; and filled (black) circles 192 represent the test sample. The total of eight black circles correspond to two salmon trout skin samples and two salmon trout meat samples, each represented by two averaged spectra. FIG. 19B shows results of samlet sample identification. Filled (black) circles 193 represent two test samples. The total of four black circles 193 correspond to two samlet skin samples and two samlet meat samples, each represented by two averaged spectra. One can see from FIGS. 19A and 19B that samlet, both skin and meat, is readily identifiable and distinguishable from salmon trout.

Meerbarbe Filets Freshness

A numerical study of reflection spectra of meerbarbe filets has been performed, in which various known multivariate analysis methods were used to differentiate between meerbarbe filet (both skin and skinless meat) freshness conditions.

Table 1 below summarizes successful prediction rate with alternate matching methods of the mullet and red mullet performed on a typical desktop computer. The spectra were auto-scaled before being sent to multivariate pattern classifiers. The last column of Table 1 provides the time it takes to build the predictive models. The time to perform prediction based on existing models are typically in the range of milliseconds. The time to build model can become important factors when one needs to do in-situ models updating. In field, point-of-use applications, the speed of measurement and the speed of obtaining the results are important to be as short as possible. In addition, the accuracy of the results is important. From Table 1, one can see that methods such as SVM (with linear kernel) provide the best accuracy at the shortest time.

TABLE 1

| Method Name | Prediction Success Rate | Models building Time |
|---|---|---|
| Naive Bayes classifier | 83.3% | <0.1 sec |
| Classification and Regression Trees (CART) | 75% | <0.1 sec |
| TreeBagger implementation of bagged decision trees | 83.3% | 0.3 sec |
| LIBLINEAR linear classifier | 81.7% | <0.1 sec |
| Support Vector Machine (SVM) with Linear Kernel | 93.3% | <0.1 sec |
| Support Vector Machine Radial Basis Function (SVM-RBF) | 81.7% | <0.1 sec |
| Linear Discriminant Analysis (LDA) | 85% | <0.1 sec |
| Quadratic Discriminant Analysis (QDA) | 85% | <0.1 sec |
| Partial Least Squares Discriminant Analysis (PLS-DA) | 86.7% | 44 sec |
| SIMCA | 88.3% | 1 sec |

Below, the numerical methods of Table 1 are discussed only briefly, since the methods themselves are known in the art. Each of the methods has its advantages. In the Naïve Bayes method, it is assumes that all features are independent on each other, and the results can be easily interpreted. The CART method is also easy to understand and interpret; however, trees created from numeric datasets can be complex, and the method tends to have over-fitting problems. The TreeBagger Analysis and Random Forest Analysis methods usually gave very good results, and the "training" step of the method was relatively quick. LIBLINEAR method was very efficient in distinguishing seafood species and conditions. The SVM method with Linear Kernel, including Support Vector Classification (SVC) for qualitative analysis, and Support Vector Regression (SVR) for quantitative analysis, resulted in the prediction success rate of over 93%. In LDA method, it is assumed that all classes have identical covariance matrix and are normally distributed, and Discriminant functions are always linear. In QDA method, the classes do not necessarily have identical covariance matrix, but the normal distribution is still assumed. Partial Least Square (PLS) is a statistical method that bears some relation to principal components regression; instead of finding hyperplanes of minimum variance between the response and independent variables, it finds a linear regression model by projecting the predicted variables and the observable variables to a new space. Partial least squares Discriminant Analysis (PLS-DA) is a variant used when the Y is categorial. PLS-DA methods resulted in moderate prediction rates of 85-87%.

The results show that NaiveBayes, TreeBagger, SVM-linear, LDA, QDA, PLS-DA, and SIMCA can be used in the multivariate analysis for the purpose of correlating the NIR reflection spectra with seafood samples. First and second derivatives of the obtained spectra can also be used in place of, or in addition to the pretreatments of spectra, as an input data strings for the multivariate analysis.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A method comprising:
    receiving, by a mobile device, a reflection spectrum of a sample;
    providing, by the mobile device, the reflection spectrum to a remote server;
    receiving, by the mobile device and from the remote server, a result of a multivariate pattern recognition analysis that is performed by comparing a distance parameter, based on the reflection spectrum and known identity spectra corresponding to different species of seafood, to a threshold associated with a species of seafood of the different species of seafood;
    determining, by the mobile device, information regarding the sample based on receiving the result of the multivariate pattern recognition analysis; and
    providing, by the mobile device and for display, the information regarding the sample.

2. The method of claim 1, wherein receiving the result of the multivariate pattern recognition analysis comprises:
    receiving the result of the multivariate pattern recognition analysis after the remote server identifies the sample based on performing the multivariate pattern recognition analysis.

3. The method of claim 1, wherein determining the information regarding the sample comprises:
    identifying, by the mobile device and after receiving the result of the multivariate pattern recognition analysis, the sample based on the multivariate pattern recognition analysis; and
    determining the information regarding the sample based on identifying the sample.

4. The method of claim 1, wherein the mobile device receives the reflection spectrum from a portable spectrometer that is connected to the mobile device via a wireless link.

5. The method of claim 1, wherein providing the reflection spectrum to the remote server comprises:
    providing the reflection spectrum to the remote server via a cellular connection.

6. The method of claim 1, where the sample is a seafood sample.

7. The method of claim 1,
    wherein the information regarding the sample includes an identity of the sample, and
    wherein a library of the known identity spectra is generated based on collecting a first plurality of spectra for at least one seafood sample of a plurality of samples and performing an operation on the first plurality of spectra to generate a second plurality of spectra corresponding to the known identity spectra.

8. A mobile device comprising:
    one or more memories; and
    one or more processors communicatively coupled to the one or more memories, configured to:
        receive, from a spectrometer, a reflection spectrum of a sample;
        provide the reflection spectrum to a remote server;
        receive, from the remote server, a result of a multivariate pattern recognition analysis that is performed by comparing a distance parameter, based on the reflection spectrum and known identity spectra corresponding to different species of seafood, to a threshold associated with a species of seafood of the different species of seafood; and
        provide, for display, information regarding the sample based on receiving the result of the multivariate pattern recognition analysis.

9. The mobile device of claim 8, wherein the one or more processors, when receiving the result of the multivariate pattern recognition analysis, are configured to:
    receive the result of the multivariate pattern recognition analysis after the remote server identifies the sample based on performing the multivariate pattern recognition analysis.

10. The mobile device of claim 8, wherein the one or more processors are further configured to:
    identify, after receiving the result of the multivariate pattern recognition analysis, the sample based on the multivariate pattern recognition analysis.

11. The mobile device of claim 8,
    wherein the mobile device and the spectrometer are connected via a wireless link, and
    wherein the spectrometer is a portable spectrometer.

12. The mobile device of claim 8, wherein the one or more processors, when providing the reflection spectrum to the remote server, are configured to:
    provide the reflection spectrum to the remote server via a cell tower.

13. The mobile device of claim 8, where the sample is a seafood sample.

14. The mobile device of claim 8,
    wherein the information regarding the sample includes an identity of the sample, and
    wherein a library of the known identity spectra is generated based on collecting a first plurality of spectra for at least one seafood sample of a plurality of samples and performing an operation on the first plurality of spectra to generate a second plurality of spectra corresponding to the known identity spectra.

15. A non-transitory computer-readable medium storing instructions, the instructions comprising:
one or more instructions that, when executed by one or more processors, cause the one or more processors to:
receive a reflection spectrum of a sample;
provide the reflection spectrum to a remote server;
receive, from the remote server, a result of a multivariate pattern recognition analysis that is performed by comparing a distance parameter, based on the reflection spectrum and known identity spectra corresponding to different species of seafood, to a threshold associated with a species of seafood of the different species of seafood; and
provide, for display, information regarding the sample based on receiving the result of the multivariate pattern recognition analysis.

16. The non-transitory computer-readable medium of claim 15, wherein the one or more instructions, that cause the one or more processors to receive the result of the multivariate pattern recognition analysis, cause the one or more processors to:
receive the result of the multivariate pattern recognition analysis after the remote server identifies the sample based on performing the multivariate pattern recognition analysis.

17. The non-transitory computer-readable medium of claim 15, wherein the one or more instructions, when executed by the one or more processors, further cause the one or more processors to:
identify, after receiving the result of the multivariate pattern recognition analysis, the sample based on the multivariate pattern recognition analysis.

18. The non-transitory computer-readable medium of claim 15,
wherein a library of the known identity spectra is generated based on collecting a first plurality of spectra for at least one seafood sample of a plurality of samples and performing an operation on the first plurality of spectra to generate a second plurality of spectra corresponding to the known identity spectra.

19. The non-transitory computer-readable medium of claim 15, wherein the reflection spectrum is received from a portable spectrometer.

20. The non-transitory computer-readable medium of claim 19, wherein the one or more processors are included in a mobile device that is connected to the portable spectrometer via a wired link.

* * * * *